US007572893B2

(12) United States Patent
Dix et al.

(10) Patent No.: US 7,572,893 B2
(45) Date of Patent: Aug. 11, 2009

(54) IL-1 ANTAGONIST FORMULATIONS

(75) Inventors: Daniel Dix, LaGrangeville, NY (US); Katherine Bowers, Clayton, NC (US); Chimanlall Goolcharran, Hopewell Junction, NY (US); Leu-Fen H. Lin, White Plains, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 130 days.

(21) Appl. No.: 11/750,613

(22) Filed: May 18, 2007

(65) Prior Publication Data

US 2008/0015148 A1 Jan. 17, 2008

Related U.S. Application Data

(63) Continuation-in-part of application No. 11/205,935, filed on Aug. 17, 2005, now Pat. No. 7,365,165.

(60) Provisional application No. 60/602,137, filed on Aug. 17, 2004.

(51) Int. Cl.
*A61K 36/20* (2006.01)
*A61K 47/48* (2006.01)
*C07K 14/475* (2006.01)

(52) U.S. Cl. ............................ 530/351; 514/12; 514/2; 424/85.4

(58) Field of Classification Search ....................... None
See application file for complete search history.

(56) References Cited

U.S. PATENT DOCUMENTS

| | | | |
|---|---|---|---|
| 5,399,670 | A | 3/1995 | Bhattacharya et al. |
| 6,267,958 | B1 | 7/2001 | Andya et al. |
| 6,875,432 | B2 | 4/2005 | Liu et al. |
| 7,001,892 | B1 | 2/2006 | Chmielewski et al. |
| 7,060,268 | B2 | 6/2006 | Andya et al. |
| 2003/0113316 | A1 | 6/2003 | Kaisheva et al. |
| 2003/0143697 | A1 | 7/2003 | Stahl et al. |
| 2006/0217311 | A1 | 9/2006 | Dix et al. |

FOREIGN PATENT DOCUMENTS

| | | |
|---|---|---|
| WO | WO93/00807 | 1/1993 |

OTHER PUBLICATIONS

Daugherty and MRSNY, 2006, "Formulation and delivery issues for monoclonal antibody therapeutics.", Advanced Drug Delivery Reviews 58: 686-706.
Katayama et al., 2004, "Retrospective statistical analysis of lyophilized protein formulations of progenipoietin using PLS: Determination of the critical parameters for long-term storage stability." Jour. Pharm. Sci. 93(10): 2609-2623.
Carpenter et al., 1997, "Rational design of stable lyophilized protein formulations: Some practical advice." Pharm. Research 14(8): 969-975.
Chang et al., 1996, "Physical factors affecting the storage stability of freeze-dried interleukin-1 receptor antagonist: Glass transition and protein conformation." Arch. Biochem. Biophys. 331(2): 249-258.
Webb et al., 2001, "A new mechanism for decreasing aggregation of recombinant human interferon-gama by a surfactant: Slowed dissolution of lyophilized formulations in a solution containing 0.03% polysorbate 20." Jour. Pharm. Sci. 91(2): 543-558.
Wang, 1999, "Instability, stabilization, and formulation of liquid protein pharmaceuticals." International Jour. Pharmceutics 185: 129-188.
Sharma and Kalonia, 2004, "Polyethylene glycol-induced precipitation of interferon alpha-2a followed by vacuum drying: development of a novel process for obtaining a dry, stable powder." AAPS PharmSci. 6(1):1-14.
Chang et al, 1996, "Development of a stable freeze-dried formulation of recombinant human interleukin-1 receptor antagonist." Pharm. Research 13(2): 243-249.

*Primary Examiner*—Bridget E Bunner
*Assistant Examiner*—Fozia M Hamud
(74) *Attorney, Agent, or Firm*—Tor Smeland, Esq.; Valeta Gregg, Esq.

(57) ABSTRACT

Formulations of an interleukin-1 (IL-1) antagonist are provided including a pre-lyophilized formulation, a reconstituted lyophilized formulation, and a stable liquid formulation. Preferably, the IL-1 antagonist is an IL-1 trap composed of a dimer of two fusion protein having an amino acid sequence selected from the group consisting of SEQ ID NO: 10.

19 Claims, 3 Drawing Sheets

SEQUENCE LISTING

```
<160> NUMBER OF SEQ ID NOS: 26

<210> SEQ ID NO 1
<211> LENGTH: 2733
<212> TYPE: DNA
<213> ORGANISM: Homo sapiens

<400> SEQUENCE: 1

atggtgcttc tgtggtgtgt agtgagtctc tacttttatg gaatcctgca aagtgatgcc      60

tcagaacgct gcgatgactg gggactagac accatgaggc aaatccaagt gtttgaagat     120
```

-continued

```
gagccagctc gcatcaagtg cccactcttt gaacacttct tgaaattcaa ctacagcaca    180
gcccattcag ctggccttac tctgatctgg tattggacta ggcaggaccg ggaccttgag    240
gagccaatta acttccgcct ccccgagaac cgcattagta aggagaaaga tgtgctgtgg    300
ttccggccca ctctcctcaa tgacactggc aactatacct gcatgttaag gaacactaca    360
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc caagatacac agtgtccggt   1080
ggcgcgccta tgctgagcga ggctgataaa tgcaaggaac gtgaagaaaa aataatttta   1140
gtgtcatctg caaatgaaat tgatgttcgt ccctgtcctc ttaacccaaa tgaacacaaa   1200
ggcactataa cttggtataa ggatgacagc aagacacctg tatctacaga acaagcctcc   1260
aggattcatc aacacaaaga gaaactttgg tttgttcctg ctaaggtgga ggattcagga   1320
cattactatt gcgtggtaag aaattcatct tactgcctca gaattaaaat aagtgcaaaa   1380
tttgtggaga atgagcctaa cttatgttat aatgcacaag ccatatttaa gcagaaacta   1440
cccgttgcag gagacggagg acttgtgtgc ccttatatgg agtttttttaa aaatgaaaat   1500
aatgagttac ctaaattaca gtggtataag gattgcaaac ctctacttct tgacaatata   1560
cactttagtg gagtcaaaga taggctcatc gtgatgaatg tggctgaaaa gcatagaggg   1620
aactatactt gtcatgcatc ctacacatac ttgggcaagc aatatcctat tacccgggta   1680
atagaattta ttactctaga ggaaaacaaa cccacaaggc ctgtgattgt gagcccagct   1740
aatgagacaa tggaagtaga cttgggatcc cagatacaat tgatctgtaa tgtcaccggc   1800
cagttgagtg acattgctta ctggaagtgg aatgggtcag taattgatga agatgaccca   1860
gtgctagggg aagactatta cagtgtggaa aatcctgcaa acaaaaagaag gagtaccctc   1920
atcacagtgc ttaatatatc ggaaattgag agtagatttt ataaacatcc atttacctgt   1980
tttgccaaga atacacatgg tatagatgca gcatatatcc agttaatata tccagtcact   2040
aattccggag acaaaactca cacatgccca ccgtgcccag cacctgaact cctgggggga   2100
ccgtcagtct tcctcttccc cccaaaaccc aaggacaccc tcatgatctc ccggacccct   2160
gaggtcacat gcgtggtggt ggacgtgagc cacgaagacc ctgaggtcaa gttcaactgg   2220
tacgtggacg gcgtggaggt gcataatgcc aagacaaagc cgcgggagga gcagtacaac   2280
agcacgtacc gtgtggtcag cgtcctcacc gtcctgcacc aggactggct gaatggcaag   2340
gagtacaagt gcaaggtctc caacaaagcc ctcccagccc ccatcgagaa aaccatctcc   2400
aaagccaaag ggcagccccg agaaccacag gtgtacaccc tgcccccatc ccgggaggag   2460
```

-continued

```
atgaccaaga accaggtcag cctgacctgc ctggtcaaag gcttctatcc cagcgacatc   2520

gccgtggagt gggagagcaa tgggcagccg gagaacaact acaagaccac gcctcccgtg   2580

ctggactccg acggctcctt cttcctctat agcaagctca ccgtggacaa gagcaggtgg   2640

cagcagggga acgtcttctc atgctccgtg atgcatgagg ctctgcacaa ccactacacg   2700

cagaagagcc tctccctgtc tccgggtaaa tga                                2733


<210> SEQ ID NO 2
<211> LENGTH: 910
<212> TYPE: PRT
<213> ORGANISM: Homo sapiens

<400> SEQUENCE: 2

Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
```

-continued

```
                325                 330                 335

Ala Lys Gly Glu Val Ala Lys Ala Ala Lys Val Lys Gln Lys Val Pro
            340                 345                 350

Ala Pro Arg Tyr Thr Val Ser Gly Gly Ala Pro Met Leu Ser Glu Ala
        355                 360                 365

Asp Lys Cys Lys Glu Arg Glu Glu Lys Ile Ile Leu Val Ser Ser Ala
    370                 375                 380

Asn Glu Ile Asp Val Arg Pro Cys Pro Leu Asn Pro Asn Glu His Lys
385                 390                 395                 400

Gly Thr Ile Thr Trp Tyr Lys Asp Asp Ser Lys Thr Pro Val Ser Thr
                405                 410                 415

Glu Gln Ala Ser Arg Ile His Gln His Lys Glu Lys Leu Trp Phe Val
            420                 425                 430

Pro Ala Lys Val Glu Asp Ser Gly His Tyr Tyr Cys Val Val Arg Asn
        435                 440                 445

Ser Ser Tyr Cys Leu Arg Ile Lys Ile Ser Ala Lys Phe Val Glu Asn
    450                 455                 460

Glu Pro Asn Leu Cys Tyr Asn Ala Gln Ala Ile Phe Lys Gln Lys Leu
465                 470                 475                 480

Pro Val Ala Gly Asp Gly Gly Leu Val Cys Pro Tyr Met Glu Phe Phe
                485                 490                 495

Lys Asn Glu Asn Asn Glu Leu Pro Lys Leu Gln Trp Tyr Lys Asp Cys
            500                 505                 510

Lys Pro Leu Leu Leu Asp Asn Ile His Phe Ser Gly Val Lys Asp Arg
        515                 520                 525

Leu Ile Val Met Asn Val Ala Glu Lys His Arg Gly Asn Tyr Thr Cys
    530                 535                 540

His Ala Ser Tyr Thr Tyr Leu Gly Lys Gln Tyr Pro Ile Thr Arg Val
545                 550                 555                 560

Ile Glu Phe Ile Thr Leu Glu Glu Asn Lys Pro Thr Arg Pro Val Ile
                565                 570                 575

Val Ser Pro Ala Asn Glu Thr Met Glu Val Asp Leu Gly Ser Gln Ile
            580                 585                 590

Gln Leu Ile Cys Asn Val Thr Gly Gln Leu Ser Asp Ile Ala Tyr Trp
        595                 600                 605

Lys Trp Asn Gly Ser Val Ile Asp Glu Asp Asp Pro Val Leu Gly Glu
    610                 615                 620

Asp Tyr Tyr Ser Val Glu Asn Pro Ala Asn Lys Arg Arg Ser Thr Leu
625                 630                 635                 640

Ile Thr Val Leu Asn Ile Ser Glu Ile Glu Ser Arg Phe Tyr Lys His
                645                 650                 655

Pro Phe Thr Cys Phe Ala Lys Asn Thr His Gly Ile Asp Ala Ala Tyr
            660                 665                 670

Ile Gln Leu Ile Tyr Pro Val Thr Asn Ser Gly Asp Lys Thr His Thr
        675                 680                 685

Cys Pro Pro Cys Pro Ala Pro Glu Leu Leu Gly Gly Pro Ser Val Phe
    690                 695                 700

Leu Phe Pro Pro Lys Pro Lys Asp Thr Leu Met Ile Ser Arg Thr Pro
705                 710                 715                 720

Glu Val Thr Cys Val Val Val Asp Val Ser His Glu Asp Pro Glu Val
                725                 730                 735

Lys Phe Asn Trp Tyr Val Asp Gly Val Glu Val His Asn Ala Lys Thr
            740                 745                 750
```

-continued

```
Lys Pro Arg Glu Glu Gln Tyr Asn Ser Thr Tyr Arg Val Val Ser Val
        755                 760                 765

Leu Thr Val Leu His Gln Asp Trp Leu Asn Gly Lys Glu Tyr Lys Cys
    770                 775                 780

Lys Val Ser Asn Lys Ala Leu Pro Ala Pro Ile Glu Lys Thr Ile Ser
785                 790                 795                 800

Lys Ala Lys Gly Gln Pro Arg Glu Pro Gln Val Tyr Thr Leu Pro Pro
                805                 810                 815

Ser Arg Glu Glu Met Thr Lys Asn Gln Val Ser Leu Thr Cys Leu Val
            820                 825                 830

Lys Gly Phe Tyr Pro Ser Asp Ile Ala Val Glu Trp Glu Ser Asn Gly
        835                 840                 845

Gln Pro Glu Asn Asn Tyr Lys Thr Thr Pro Pro Val Leu Asp Ser Asp
    850                 855                 860

Gly Ser Phe Phe Leu Tyr Ser Lys Leu Thr Val Asp Lys Ser Arg Trp
865                 870                 875                 880

Gln Gln Gly Asn Val Phe Ser Cys Ser Val Met His Glu Ala Leu His
                885                 890                 895

Asn His Tyr Thr Gln Lys Ser Leu Ser Leu Ser Pro Gly Lys
            900                 905                 910


<210> SEQ ID NO 3
<211> LENGTH: 2703
<212> TYPE: DNA
<213> ORGANISM: Homo sapiens

<400> SEQUENCE: 3

atggtgttac tcagacttat ttgtttcata gctctactga tttcttctct ggaggctgat     60

aaatgcaagg aacgtgaaga aaaaataatt ttagtgtcat ctgcaaatga aattgatgtt    120

cgtccctgtc ctcttaaccc aaatgaacac aaaggcacta taacttggta taaggatgac    180

agcaagacac ctgtatctac agaacaagcc tccaggattc atcaacacaa agagaaactt    240

tggtttgttc ctgctaaggt ggaggattca ggacattact attgcgtggt aagaaattca    300

tcttactgcc tcagaattaa aataagtgca aaatttgtgg agaatgagcc taacttatgt    360

tataatgcac aagccatatt taagcagaaa ctacccgttg caggagacgg aggacttgtg    420

tgcccttata tggagttttt taaaaatgaa aataatgagt tacctaaatt acagtggtat    480

aaggattgca aacctctact tcttgacaat atacacttta gtggagtcaa agataggctc    540

atcgtgatga atgtggctga aaagcataga gggaactata cttgtcatgc atcctacaca    600

tacttgggca agcaatatcc tattacccgg gtaatagaat ttattactct agaggaaaac    660

aaacccacaa ggcctgtgat tgtgagccca gctaatgaga caatggaagt agacttggga    720

tcccagatac aattgatctg taatgtcacc ggccagttga gtgacattgc ttactggaag    780

tggaatgggt cagtaattga tgaagatgac ccagtgctag gggaagacta ttacagtgtg    840

gaaaatcctg caaacaaaag aaggagtacc ctcatcacag tgcttaatat atcggaaatt    900

gagagtagat tttataaaca tccatttacc tgttttgcca agaatacaca tggtatagat    960

gcagcatata tccagttaat atatccagtc actaattcag aacgctgcga tgactgggga   1020

ctagacacca tgaggcaaat ccaagtgttt gaagatgagc cagctcgcat caagtgccca   1080

ctctttgaac acttcttgaa attcaactac agcacagccc attcagctgg ccttactctg   1140

atctggtatt ggactaggca ggaccgggac cttgaggagc caattaactt ccgcctcccc   1200
```

-continued

```
gagaaccgca ttagtaagga gaaagatgtg ctgtggttcc ggcccactct cctcaatgac   1260

actggcaact atacctgcat gttaaggaac actacatatt gcagcaaagt tgcatttccc   1320

ttggaagttg ttcaaaaaga cagctgtttc aattccccca tgaaactccc agtgcataaa   1380

ctgtatatag aatatggcat tcagaggatc acttgtccaa atgtagatgg atattttcct   1440

tccagtgtca aaccgactat cacttggtat atgggctgtt ataaaataca gaattttaat   1500

aatgtaatac ccgaaggtat gaacttgagt ttcctcattg ccttaatttc aaataatgga   1560

aattacacat gtgttgttac atatccagaa aatggacgta cgtttcatct caccaggact   1620

ctgactgtaa aggtagtagg ctctccaaaa aatgcagtgc cccctgtgat ccattcacct   1680

aatgatcatg tggtctatga gaaagaacca ggagaggagc tactcattcc ctgtacggtc   1740

tattttagtt ttctgatgga ttctcgcaat gaggtttggt ggaccattga tggaaaaaaa   1800

cctgatgaca tcactattga tgtcaccatt aacgaaagta taagtcatag tagaacagaa   1860

gatgaaacaa gaactcagat tttgagcatc aagaaagtta cctctgagga tctcaagcgc   1920

agctatgtct gtcatgctag aagtgccaaa ggcgaagttg ccaaagcagc caaggtgaag   1980

cagaaagtgc cagctccaag atacacagtg gaatccggag acaaaactca cacatgccca   2040

ccgtgcccag cacctgaact cctgggggga ccgtcagtct tcctcttccc cccaaaaccc   2100

aaggacaccc tcatgatctc ccggacccct gaggtcacat gcgtggtggt ggacgtgagc   2160

cacgaagacc ctgaggtcaa gttcaactgg tacgtggacg gcgtggaggt gcataatgcc   2220

aagacaaagc cgcgggagga gcagtacaac agcacgtacc gtgtggtcag cgtcctcacc   2280

gtcctgcacc aggactggct gaatggcaag gagtacaagt gcaaggtctc caacaaagcc   2340

ctcccagccc ccatcgagaa aaccatctcc aaagccaaag ggcagccccg agaaccacag   2400

gtgtacaccc tgcccccatc ccgggaggag atgaccaaga accaggtcag cctgacctgc   2460

ctggtcaaag gcttctatcc cagcgacatc gccgtggagt gggagagcaa tgggcagccg   2520

gagaacaact acaagaccac gcctcccgtg ctggactccg acggctcctt cttcctctat   2580

agcaagctca ccgtggacaa gagcaggtgg cagcagggga acgtcttctc atgctccgtg   2640

atgcatgagg ctctgcacaa ccactacacg cagaagagcc tctccctgtc tccgggtaaa   2700

tga                                                                 2703
```

<210> SEQ ID NO 4
<211> LENGTH: 900
<212> TYPE: PRT
<213> ORGANISM: Homo sapiens

<400> SEQUENCE: 4

```
Met Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
```

-continued

```
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
        515                 520                 525
```

-continued

```
Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Asp Lys Thr His Thr Cys Pro Pro Cys Pro Ala Pro Glu Leu Leu
        675                 680                 685

Gly Gly Pro Ser Val Phe Leu Phe Pro Pro Lys Pro Lys Asp Thr Leu
    690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
            740                 745                 750

Tyr Arg Val Val Ser Val Leu Thr Val Leu His Gln Asp Trp Leu Asn
        755                 760                 765

Gly Lys Glu Tyr Lys Cys Lys Val Ser Asn Lys Ala Leu Pro Ala Pro
    770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Glu Glu Met Thr Lys Asn Gln Val
                805                 810                 815

Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
        835                 840                 845

Pro Val Leu Asp Ser Asp Gly Ser Phe Phe Leu Tyr Ser Lys Leu Thr
    850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900
```

<210> SEQ ID NO 5
<211> LENGTH: 2709
<212> TYPE: DNA
<213> ORGANISM: Homo sapiens -continued

<400> SEQUENCE: 5

```
atggtgttac tcagacttat ttgtttcata gctctactga tttcttctct ggaggctgat      60
aaatgcaagg aacgtgaaga aaaaataatt ttagtgtcat ctgcaaatga aattgatgtt     120
cgtccctgtc ctcttaaccc aaatgaacac aaaggcacta taacttggta taaggatgac     180
agcaagacac ctgtatctac agaacaagcc tccaggattc atcaacacaa agagaaactt     240
tggtttgttc ctgctaaggt ggaggattca ggacattact attgcgtggt aagaaattca     300
tcttactgcc tcagaattaa aataagtgca aaatttgtgg agaatgagcc taacttatgt     360
tataatgcac aagccatatt taagcagaaa ctacccgttg caggagacgg aggacttgtg     420
tgcccttata tggagttttt taaaaatgaa aataatgagt tacctaaatt acagtggtat     480
aaggattgca aacctctact tcttgacaat atacacttta gtggagtcaa agataggctc     540
atcgtgatga atgtggctga aaagcataga gggaactata cttgtcatgc atcctacaca     600
tacttgggca agcaatatcc tattacccgg gtaatagaat ttattactct agaggaaaac     660
aaacccacaa ggcctgtgat tgtgagccca gctaatgaga caatggaagt agacttggga     720
tcccagatac aattgatctg taatgtcacc ggccagttga gtgacattgc ttactggaag     780
tggaatgggt cagtaattga tgaagatgac ccagtgctag gggaagacta ttacagtgtg     840
gaaaatcctg caaacaaaag aaggagtacc ctcatcacag tgcttaatat atcggaaatt     900
gagagtagat tttataaaca tccatttacc tgttttgcca agaatacaca tggtatagat     960
gcagcatata tccagttaat atatccagtc actaattcag aacgctgcga tgactgggga    1020
ctagacacca tgaggcaaat ccaagtgttt gaagatgagc cagctcgcat caagtgccca    1080
ctctttgaac acttcttgaa attcaactac agcacagccc attcagctgg ccttactctg    1140
atctggtatt ggactaggca ggaccgggac cttgaggagc caattaactt ccgcctcccc    1200
gagaaccgca ttagtaagga gaaagatgtg ctgtggttcc ggcccactct cctcaatgac    1260
actggcaact atacctgcat gttaaggaac actacatatt gcagcaaagt tgcatttccc    1320
ttggaagttg ttcaaaaaga cagctgtttc aattccccca tgaaactccc agtgcataaa    1380
ctgtatatag aatatggcat tcagaggatc acttgtccaa atgtagatgg atattttcct    1440
tccagtgtca aaccgactat cacttggtat atgggctgtt ataaaataca gaattttaat    1500
aatgtaatac ccgaaggtat gaacttgagt ttcctcattg ccttaatttc aaataatgga    1560
aattacacat gtgttgttac atatccagaa aatggacgta cgtttcatct caccaggact    1620
ctgactgtaa aggtagtagg ctctccaaaa aatgcagtgc cccctgtgat ccattcacct    1680
aatgatcatg tggtctatga gaaagaacca ggagaggagc tactcattcc ctgtacggtc    1740
tattttagtt ttctgatgga ttctcgcaat gaggtttggt ggaccattga tggaaaaaaa    1800
cctgatgaca tcactattga tgtcaccatt aacgaaagta taagtcatag tagaacagaa    1860
gatgaaacaa gaactcagat tttgagcatc aagaaagtta cctctgagga tctcaagcgc    1920
agctatgtct gtcatgctag aagtgccaaa ggcgaagttg ccaaagcagc caaggtgaag    1980
cagaaagtgc cagctccaag atacacagtg gaatccggag agtccaaata cggtccgcca    2040
tgcccatcat gcccagcacc tgagttcctg gggggaccat cagtcttcct gttcccccca    2100
aaacccaagg acactctcat gatctcccgg acccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
```

-continued aaaggcctcc cgtcctccat cgagaaaacc atctccaaag ccaaagggca gccccgagag 2400
ccacaggtgt acaccctgcc cccatcccag gaggagatga ccaagaacca ggtcagcctg 2460
acctgcctgg tcaaaggctt ctaccccagc gacatcgccg tggagtggga gagcaatggg 2520
cagccggaga acaactacaa gaccacgcct cccgtgctgg actccgacgg ctccttcttc 2580
ctctacagca ggctaaccgt ggacaagagc aggtggcagg aggggaatgt cttctcatgc 2640
tccgtgatgc atgaggctct gcacaaccac tacacacaga agagcctctc cctgtctctg 2700
ggtaaatga 2709

<210> SEQ ID NO 6
<211> LENGTH: 902
<212> TYPE: PRT
<213> ORGANISM: Homo sapiens

<400> SEQUENCE: 6

Met Val Leu Leu Arg Leu Ile Cys Phe Ile Ala Leu Leu Ile Ser Ser
1 5 10 15

Leu Glu Ala Asp Lys Cys Lys Glu Arg Glu Glu Lys Ile Ile Leu Val
20 25 30

Ser Ser Ala Asn Glu Ile Asp Val Arg Pro Cys Pro Leu Asn Pro Asn
35 40 45

Glu His Lys Gly Thr Ile Thr Trp Tyr Lys Asp Asp Ser Lys Thr Pro
50 55 60

Val Ser Thr Glu Gln Ala Ser Arg Ile His Gln His Lys Glu Lys Leu
65 70 75 80

Trp Phe Val Pro Ala Lys Val Glu Asp Ser Gly His Tyr Tyr Cys Val
85 90 95

Val Arg Asn Ser Ser Tyr Cys Leu Arg Ile Lys Ile Ser Ala Lys Phe
100 105 110

Val Glu Asn Glu Pro Asn Leu Cys Tyr Asn Ala Gln Ala Ile Phe Lys
115 120 125

Gln Lys Leu Pro Val Ala Gly Asp Gly Gly Leu Val Cys Pro Tyr Met
130 135 140

Glu Phe Phe Lys Asn Glu Asn Asn Glu Leu Pro Lys Leu Gln Trp Tyr
145 150 155 160

Lys Asp Cys Lys Pro Leu Leu Leu Asp Asn Ile His Phe Ser Gly Val
165 170 175

Lys Asp Arg Leu Ile Val Met Asn Val Ala Glu Lys His Arg Gly Asn
180 185 190

Tyr Thr Cys His Ala Ser Tyr Thr Tyr Leu Gly Lys Gln Tyr Pro Ile
195 200 205

Thr Arg Val Ile Glu Phe Ile Thr Leu Glu Glu Asn Lys Pro Thr Arg
210 215 220

Pro Val Ile Val Ser Pro Ala Asn Glu Thr Met Glu Val Asp Leu Gly
225 230 235 240

Ser Gln Ile Gln Leu Ile Cys Asn Val Thr Gly Gln Leu Ser Asp Ile
245 250 255

Ala Tyr Trp Lys Trp Asn Gly Ser Val Ile Asp Glu Asp Asp Pro Val
260 265 270

Leu Gly Glu Asp Tyr Tyr Ser Val Glu Asn Pro Ala Asn Lys Arg Arg
275 280 285

Ser Thr Leu Ile Thr Val Leu Asn Ile Ser Glu Ile Glu Ser Arg Phe
290 295 300

-continued

```
Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
        515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Glu Ser Lys Tyr Gly Pro Pro Cys Pro Ser Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720
```

-continued

```
Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900


<210> SEQ ID NO 7
<211> LENGTH: 2709
<212> TYPE: DNA
<213> ORGANISM: Homo sapiens

<400> SEQUENCE: 7

atggtgttac tcagacttat ttgtttcata gctctactga tttcttctct ggaggctgat      60

aaatgcaagg aacgtgaaga aaaaataatt ttagtgtcat ctgcaaatga aattgatgtt     120

cgtccctgtc ctcttaaccc aaatgaacac aaaggcacta taacttggta taaggatgac     180

agcaagacac ctgtatctac agaacaagcc tccaggattc atcaacacaa agagaaactt     240

tggtttgttc ctgctaaggt ggaggattca ggacattact attgcgtggt aagaaattca     300

tcttactgcc tcagaattaa aataagtgca aaatttgtgg agaatgagcc taacttatgt     360

tataatgcac aagccatatt taagcagaaa ctacccgttg caggagacgg aggacttgtg     420

tgcccttata tggagttttt taaaaatgaa aataatgagt tacctaaatt acagtggtat     480

aaggattgca aacctctact tcttgacaat atacacttta gtggagtcaa agataggctc     540

atcgtgatga atgtggctga aaagcataga gggaactata cttgtcatgc atcctacaca     600

tacttgggca agcaatatcc tattacccgg gtaatagaat ttattactct agaggaaaac     660

aaacccacaa ggcctgtgat tgtgagccca gctaatgaga caatggaagt agacttggga     720

tcccagatac aattgatctg taatgtcacc ggccagttga gtgacattgc ttactggaag     780

tggaatgggt cagtaattga tgaagatgac ccagtgctag gggaagacta ttacagtgtg     840

gaaaatcctg caaacaaaag aaggagtacc ctcatcacag tgcttaatat atcggaaatt     900

gagagtagat tttataaaca tccatttacc tgttttgcca agaatacaca tggtatagat     960

gcagcatata tccagttaat atatccagtc actaattcag aacgctgcga tgactgggga    1020

ctagacacca tgaggcaaat ccaagtgttt gaagatgagc cagctcgcat caagtgccca    1080
```

ctctttgaac acttcttgaa attcaactac agcacagccc attcagctgg ccttactctg 1140
atctggtatt ggactaggca ggaccgggac cttgaggagc caattaactt ccgcctcccc 1200
gagaaccgca ttagtaagga gaaagatgtg ctgtggttcc ggcccactct cctcaatgac 1260
actggcaact atacctgcat gttaaggaac actacatatt gcagcaaagt tgcatttccc 1320
ttggaagttg ttcaaaaaga cagctgtttc aattccccca tgaaactccc agtgcataaa 1380
ctgtatatag aatatggcat tcagaggatc acttgtccaa atgtagatgg atattttcct 1440
tccagtgtca aaccgactat cacttggtat atgggctgtt ataaaataca gaattttaat 1500
aatgtaatac ccgaaggtat gaacttgagt ttcctcattg ccttaatttc aaataatgga 1560
aattacacat gtgttgttac atatccagaa aatggacgta cgtttcatct caccaggact 1620
ctgactgtaa aggtagtagg ctctccaaaa aatgcagtgc cccctgtgat ccattcacct 1680
aatgatcatg tggtctatga gaaagaacca ggagaggagc tactcattcc ctgtacggtc 1740
tattttagtt ttctgatgga ttctcgcaat gaggtttggt ggaccattga tggaaaaaaa 1800
cctgatgaca tcactattga tgtcaccatt aacgaaagta taagtcatag tagaacagaa 1860
gatgaaacaa gaactcagat tttgagcatc aagaaagtta cctctgagga tctcaagcgc 1920
agctatgtct gtcatgctag aagtgccaaa ggcgaagttg ccaaagcagc caaggtgaag 1980
cagaaagtgc cagctccaag atacacagtg gaatccggag agtccaaata cggtccgcca 2040
tgcccaccat gcccagcacc tgagttcctg gggggaccat cagtcttcct gttcccccca 2100
aaacccaagg acactctcat gatctcccgg acccctgagg tcacgtgcgt ggtggtggac 2160
gtgagccagg aagaccccga ggtccagttc aactggtacg tggatggcgt ggaggtgcat 2220
aatgccaaga caaagccgcg ggaggagcag ttcaacagca cgtaccgtgt ggtcagcgtc 2280
ctcaccgtcc tgcaccagga ctggctgaac ggcaaggagt acaagtgcaa ggtctccaac 2340
aaaggcctcc cgtcctccat cgagaaaacc atctccaaag ccaaagggca gccccgagag 2400
ccacaggtgt acaccctgcc cccatcccag gaggagatga ccaagaacca ggtcagcctg 2460
acctgcctgg tcaaaggctt ctaccccagc gacatcgccg tggagtggga gagcaatggg 2520
cagccggaga acaactacaa gaccacgcct cccgtgctgg actccgacgg ctccttcttc 2580
ctctacagca ggctaaccgt ggacaagagc aggtggcagg aggggaatgt cttctcatgc 2640
tccgtgatgc atgaggctct gcacaaccac tacacacaga agagcctctc cctgtctctg 2700
ggtaaatga 2709

<210> SEQ ID NO 8
<211> LENGTH: 902
<212> TYPE: PRT
<213> ORGANISM: Homo sapiens

<400> SEQUENCE: 8

Met Val Leu Leu Arg Leu Ile Cys Phe Ile Ala Leu Leu Ile Ser Ser
1 5 10 15

Leu Glu Ala Asp Lys Cys Lys Glu Arg Glu Glu Lys Ile Ile Leu Val
20 25 30

Ser Ser Ala Asn Glu Ile Asp Val Arg Pro Cys Pro Leu Asn Pro Asn
35 40 45

Glu His Lys Gly Thr Ile Thr Trp Tyr Lys Asp Asp Ser Lys Thr Pro
50 55 60

Val Ser Thr Glu Gln Ala Ser Arg Ile His Gln His Lys Glu Lys Leu
65 70 75 80

-continued

Trp Phe Val Pro Ala Lys Val Glu Asp Ser Gly His Tyr Tyr Cys Val
85 90 95

Val Arg Asn Ser Ser Tyr Cys Leu Arg Ile Lys Ile Ser Ala Lys Phe
100 105 110

Val Glu Asn Glu Pro Asn Leu Cys Tyr Asn Ala Gln Ala Ile Phe Lys
115 120 125

Gln Lys Leu Pro Val Ala Gly Asp Gly Gly Leu Val Cys Pro Tyr Met
130 135 140

Glu Phe Phe Lys Asn Glu Asn Asn Glu Leu Pro Lys Leu Gln Trp Tyr
145 150 155 160

Lys Asp Cys Lys Pro Leu Leu Leu Asp Asn Ile His Phe Ser Gly Val
165 170 175

Lys Asp Arg Leu Ile Val Met Asn Val Ala Glu Lys His Arg Gly Asn
180 185 190

Tyr Thr Cys His Ala Ser Tyr Thr Tyr Leu Gly Lys Gln Tyr Pro Ile
195 200 205

Thr Arg Val Ile Glu Phe Ile Thr Leu Glu Glu Asn Lys Pro Thr Arg
210 215 220

Pro Val Ile Val Ser Pro Ala Asn Glu Thr Met Glu Val Asp Leu Gly
225 230 235 240

Ser Gln Ile Gln Leu Ile Cys Asn Val Thr Gly Gln Leu Ser Asp Ile
245 250 255

Ala Tyr Trp Lys Trp Asn Gly Ser Val Ile Asp Glu Asp Asp Pro Val
260 265 270

Leu Gly Glu Asp Tyr Tyr Ser Val Glu Asn Pro Ala Asn Lys Arg Arg
275 280 285

Ser Thr Leu Ile Thr Val Leu Asn Ile Ser Glu Ile Glu Ser Arg Phe
290 295 300

Tyr Lys His Pro Phe Thr Cys Phe Ala Lys Asn Thr His Gly Ile Asp
305 310 315 320

Ala Ala Tyr Ile Gln Leu Ile Tyr Pro Val Thr Asn Ser Glu Arg Cys
325 330 335

Asp Asp Trp Gly Leu Asp Thr Met Arg Gln Ile Gln Val Phe Glu Asp
340 345 350

Glu Pro Ala Arg Ile Lys Cys Pro Leu Phe Glu His Phe Leu Lys Phe
355 360 365

Asn Tyr Ser Thr Ala His Ser Ala Gly Leu Thr Leu Ile Trp Tyr Trp
370 375 380

Thr Arg Gln Asp Arg Asp Leu Glu Glu Pro Ile Asn Phe Arg Leu Pro
385 390 395 400

Glu Asn Arg Ile Ser Lys Glu Lys Asp Val Leu Trp Phe Arg Pro Thr
405 410 415

Leu Leu Asn Asp Thr Gly Asn Tyr Thr Cys Met Leu Arg Asn Thr Thr
420 425 430

Tyr Cys Ser Lys Val Ala Phe Pro Leu Glu Val Val Gln Lys Asp Ser
435 440 445

Cys Phe Asn Ser Pro Met Lys Leu Pro Val His Lys Leu Tyr Ile Glu
450 455 460

Tyr Gly Ile Gln Arg Ile Thr Cys Pro Asn Val Asp Gly Tyr Phe Pro
465 470 475 480

Ser Ser Val Lys Pro Thr Ile Thr Trp Tyr Met Gly Cys Tyr Lys Ile
485 490 495

-continued

```
Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
        515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Glu Ser Lys Tyr Gly Pro Pro Cys Pro Pro Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900
```

-continued

<210> SEQ ID NO 9
<211> LENGTH: 2703
<212> TYPE: DNA
<213> ORGANISM: Homo sapiens

<400> SEQUENCE: 9
atggtgcttc tgtggtgtgt agtgagtctc tacttttatg gaatcctgca aagtgatgcc 60
tcagaacgct gcgatgactg gggactagac accatgaggc aaatccaagt gtttgaagat 120
gagccagctc gcatcaagtg cccactcttt gaacacttct tgaaattcaa ctacagcaca 180
gcccattcag ctggccttac tctgatctgg tattggacta ggcaggaccg ggaccttgag 240
gagccaatta acttccgcct ccccgagaac cgcattagta aggagaaaga tgtgctgtgg 300
ttccggccca ctctcctcaa tgacactggc aactatacct gcatgttaag gaacactaca 360
tattgcagca aagttgcatt tcccttggaa gttgttcaaa aagacagctg tttcaattcc 420
cccatgaaac tcccagtgca taaactgtat atagaatatg gcattcagag gatcacttgt 480
ccaaatgtag atggatattt tccttccagt gtcaaaccga ctatcacttg gtatatgggc 540
tgttataaaa tacagaattt taataatgta atacccgaag gtatgaactt gagtttcctc 600
attgccttaa tttcaaataa tggaaattac acatgtgttg ttacatatcc agaaaatgga 660
cgtacgtttc atctcaccag gactctgact gtaaaggtag taggctctcc aaaaaatgca 720
gtgccccctg tgatccattc acctaatgat catgtggtct atgagaaaga accaggagag 780
gagctactca ttccctgtac ggtctatttt agttttctga tggattctcg caatgaggtt 840
tggtggacca ttgatggaaa aaaacctgat gacatcacta ttgatgtcac cattaacgaa 900
agtataagtc atagtagaac agaagatgaa acaagaactc agattttgag catcaagaaa 960
gttacctctg aggatctcaa gcgcagctat gtctgtcatg ctagaagtgc caaaggcgaa 1020
gttgccaaag cagccaaggt gaagcagaaa gtgccagctc caagatacac agtggaaaaa 1080
tgcaaggaac gtgaagaaaa aataatttta gtgagctcag caaatgaaat cgatgttcgt 1140
ccctgtcctc ttaacccaaa tgaacacaaa ggcactataa cttggtataa ggatgacagc 1200
aagacacctg tatctacaga acaagcctcc aggattcatc aacacaaaga gaaactttgg 1260
tttgttcctg ctaaggtgga ggattcagga cattactatt gcgtggtaag aaattcatct 1320
tactgcctca gaattaaaat aagtgcaaaa tttgtggaga atgagcctaa cttatgttat 1380
aatgcacaag ccatatttaa gcagaaacta cccgttgcag gagacggagg acttgtgtgc 1440
ccttatatgg agttttttaa aaatgaaaat aatgagttac ctaaattaca gtggtataag 1500
gattgcaaac ctctacttct tgacaatata cactttagtg gagtcaaaga taggctcatc 1560
gtgatgaatg tggctgaaaa gcatagaggg aactatactt gtcatgcatc ctacacatac 1620
ttgggcaagc aatatcctat tacccgggta atagaattta ttactctaga ggaaaacaaa 1680
cccacaaggc ctgtgattgt gagcccagct aatgagacaa tggaagtaga cttgggatcc 1740
cagatacaat tgatctgtaa tgtcaccggc cagttgagtg acattgctta ctggaagtgg 1800
aatgggtcag taattgatga agatgaccca gtgctagggg aagactatta cagtgtggaa 1860
aatcctgcaa acaaaagaag gagtaccctc atcacagtgc ttaatatatc ggaaattgag 1920
agtagatttt ataaacatcc atttacctgt tttgccaaga atacacatgg tatagatgca 1980
gcatatatcc agttaatata tccagtcact aattccggag acaaaactca cacatgccca 2040
ccgtgcccag cacctgaact cctgggggga ccgtcagtct tcctcttccc cccaaaaccc 2100
aaggacaccc tcatgatctc ccggacccct gaggtcacat gcgtggtggt ggacgtgagc 2160

-continued

```
cacgaagacc ctgaggtcaa gttcaactgg tacgtggacg gcgtggaggt gcataatgcc   2220

aagacaaagc cgcgggagga gcagtacaac agcacgtacc gtgtggtcag cgtcctcacc   2280

gtcctgcacc aggactggct gaatggcaag gagtacaagt gcaaggtctc caacaaagcc   2340

ctcccagccc ccatcgagaa aaccatctcc aaagccaaag ggcagccccg agaaccacag   2400

gtgtacaccc tgcccccatc ccgggatgag ctgaccaaga accaggtcag cctgacctgc   2460

ctggtcaaag gcttctatcc cagcgacatc gccgtggagt gggagagcaa tgggcagccg   2520

gagaacaact acaagaccac gcctcccgtg ctggactccg acggctcctt cttcctctac   2580

agcaagctca ccgtggacaa gagcaggtgg cagcagggga acgtcttctc atgctccgtg   2640

atgcatgagg ctctgcacaa ccactacacg cagaagagcc tctccctgtc tccgggtaaa   2700

tga                                                                 2703
```

<210> SEQ ID NO 10
<211> LENGTH: 900
<212> TYPE: PRT
<213> ORGANISM: Homo sapiens

<400> SEQUENCE: 10

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270
```

-continued

```
Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Asp Lys Thr His Thr Cys Pro Pro Cys Pro Ala Pro Glu Leu Leu
        675                 680                 685

Gly Gly Pro Ser Val Phe Leu Phe Pro Pro Lys Pro Lys Asp Thr Leu
```

-continued

```
    690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
            740                 745                 750

Tyr Arg Val Val Ser Val Leu Thr Val Leu His Gln Asp Trp Leu Asn
        755                 760                 765

Gly Lys Glu Tyr Lys Cys Lys Val Ser Asn Lys Ala Leu Pro Ala Pro
    770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
                805                 810                 815

Ser Leu Thr Cys Leu Val Lys Gly Phe Tyr Pro Ser Asp Ile Ala Val
            820                 825                 830

Glu Trp Glu Ser Asn Gly Gln Pro Glu Asn Asn Tyr Lys Thr Thr Pro
        835                 840                 845

Pro Val Leu Asp Ser Asp Gly Ser Phe Phe Leu Tyr Ser Lys Leu Thr
    850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
            900


<210> SEQ ID NO 11
<211> LENGTH: 2709
<212> TYPE: DNA
<213> ORGANISM: Homo sapiens

<400> SEQUENCE: 11

atggtgcttc tgtggtgtgt agtgagtctc tacttttatg gaatcctgca aagtgatgcc     60

tcagaacgct gcgatgactg gggactagac accatgaggc aaatccaagt gtttgaagat    120

gagccagctc gcatcaagtg cccactcttt gaacacttct tgaaattcaa ctacagcaca    180

gcccattcag ctggccttac tctgatctgg tattggacta ggcaggaccg ggaccttgag    240

gagccaatta acttccgcct ccccgagaac cgcattagta aggagaaaga tgtgctgtgg    300

ttccggccca ctctcctcaa tgacactggc aactatacct gcatgttaag gaacactaca    360

tattgcagca aagttgcatt tcccttggaa gttgttcaaa aagacagctg tttcaattcc    420

cccatgaaac tcccagtgca taaactgtat atagaatatg gcattcagag gatcacttgt    480

ccaaatgtag atggatattt tccttccagt gtcaaaccga ctatcacttg gtatatgggc    540

tgttataaaa tacagaattt taataatgta atacccgaag gtatgaactt gagtttcctc    600

attgccttaa tttcaaataa tggaaattac acatgtgttg ttacatatcc agaaaatgga    660

cgtacgtttc atctcaccag gactctgact gtaaaggtag taggctctcc aaaaaatgca    720

gtgccccctg tgatccattc acctaatgat catgtggtct atgagaaaga accaggagag    780

gagctactca ttccctgtac ggtctatttt agttttctga tggattctcg caatgaggtt    840

tggtggacca ttgatggaaa aaaacctgat gacatcacta ttgatgtcac cattaacgaa    900
```

-continued agtataagtc atagtagaac agaagatgaa acaagaactc agattttgag catcaagaaa 960
gttacctctg aggatctcaa gcgcagctat gtctgtcatg ctagaagtgc caaaggcgaa 1020
gttgccaaag cagccaaggt gaagcagaaa gtgccagctc caagatacac agtggaaaaa 1080
tgcaaggaac gtgaagaaaa aataatttta gtgagctcag caaatgaaat cgatgttcgt 1140
ccctgtcctc ttaacccaaa tgaacacaaa ggcactataa cttggtataa ggatgacagc 1200
aagacacctg tatctacaga acaagcctcc aggattcatc aacacaaaga gaaactttgg 1260
tttgttcctg ctaaggtgga ggattcagga cattactatt gcgtggtaag aaattcatct 1320
tactgcctca gaattaaaat aagtgcaaaa tttgtggaga atgagcctaa cttatgttat 1380
aatgcacaag ccatatttaa gcagaaacta cccgttgcag gagacggagg acttgtgtgc 1440
ccttatatgg agttttttaa aaatgaaaat aatgagttac ctaaattaca gtggtataag 1500
gattgcaaac ctctacttct tgacaatata cactttagtg gagtcaaaga taggctcatc 1560
gtgatgaatg tggctgaaaa gcatagaggg aactatactt gtcatgcatc ctacacatac 1620
ttgggcaagc aatatcctat tacccgggta atagaattta ttactctaga ggaaaacaaa 1680
cccacaaggc ctgtgattgt gagcccagct aatgagacaa tggaagtaga cttgggatcc 1740
cagatacaat tgatctgtaa tgtcaccggc cagttgagtg acattgctta ctggaagtgg 1800
aatgggtcag taattgatga agatgaccca gtgctagggg aagactatta cagtgtggaa 1860
aatcctgcaa acaaaagaag gagtaccctc atcacagtgc ttaatatatc ggaaattgag 1920
agtagatttt ataaacatcc atttacctgt tttgccaaga atacacatgg tatagatgca 1980
gcatatatcc agttaatata tccagtcact aattccggag agtccaaata cggtccgcca 2040
tgcccatcat gcccagcacc tgagttcctg gggggaccat cagtcttcct gttcccccca 2100
aaacccaagg acactctcat gatctcccgg acccctgagg tcacgtgcgt ggtggtggac 2160
gtgagccagg aagaccccga ggtccagttc aactggtacg tggatggcgt ggaggtgcat 2220
aatgccaaga caaagccgcg ggaggagcag ttcaacagca cgtaccgtgt ggtcagcgtc 2280
ctcaccgtcc tgcaccagga ctggctgaac ggcaaggagt acaagtgcaa ggtctccaac 2340
aaaggcctcc cgtcctccat cgagaaaacc atctccaaag ccaaagggca gccccgagag 2400
ccacaggtgt acaccctgcc cccatcccag gaggagatga ccaagaacca ggtcagcctg 2460
acctgcctgg tcaaaggctt ctaccccagc gacatcgccg tggagtggga gagcaatggg 2520
cagccggaga acaactacaa gaccacgcct cccgtgctgg actccgacgg ctccttcttc 2580
ctctacagca ggctaaccgt ggacaagagc aggtggcagg aggggaatgt cttctcatgc 2640
tccgtgatgc atgaggctct gcacaaccac tacacacaga agagcctctc cctgtctctg 2700
ggtaaatga 2709

<210> SEQ ID NO 12
<211> LENGTH: 902
<212> TYPE: PRT
<213> ORGANISM: Homo sapiens

<400> SEQUENCE: 12

Met Val Leu Leu Trp Cys Val Val Ser Leu Tyr Phe Tyr Gly Ile Leu
1 5 10 15

Gln Ser Asp Ala Ser Glu Arg Cys Asp Asp Trp Gly Leu Asp Thr Met
20 25 30

Arg Gln Ile Gln Val Phe Glu Asp Glu Pro Ala Arg Ile Lys Cys Pro
35 40 45

-continued

```
Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
```

-continued

```
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670

Gly Glu Ser Lys Tyr Gly Pro Pro Cys Pro Ser Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895
```

-continued

Ser Leu Ser Leu Gly Lys
900

<210> SEQ ID NO 13
<211> LENGTH: 2709
<212> TYPE: DNA
<213> ORGANISM: Homo sapiens

<400> SEQUENCE: 13
atggtgcttc tgtggtgtgt agtgagtctc tacttttatg gaatcctgca aagtgatgcc 60
tcagaacgct gcgatgactg gggactagac accatgaggc aaatccaagt gtttgaagat 120
gagccagctc gcatcaagtg cccactcttt gaacacttct tgaaattcaa ctacagcaca 180
gcccattcag ctggccttac tctgatctgg tattggacta ggcaggaccg ggaccttgag 240
gagccaatta acttccgcct ccccgagaac cgcattagta aggagaaaga tgtgctgtgg 300
ttccggccca ctctcctcaa tgacactggc aactatacct gcatgttaag gaacactaca 360
tattgcagca aagttgcatt tcccttggaa gttgttcaaa aagacagctg tttcaattcc 420
cccatgaaac tcccagtgca taaactgtat atagaatatg gcattcagag gatcacttgt 480
ccaaatgtag atggatattt tccttccagt gtcaaaccga ctatcacttg gtatatgggc 540
tgttataaaa tacagaattt taataatgta atacccgaag gtatgaactt gagtttcctc 600
attgccttaa tttcaaataa tggaaattac acatgtgttg ttacatatcc agaaaatgga 660
cgtacgtttc atctcaccag gactctgact gtaaaggtag taggctctcc aaaaaatgca 720 gtgcccccctg tgatccattc acctaatgat catgtggtct atgagaaaga accaggagag 780
gagctactca ttccctgtac ggtctatttt agttttctga tggattctcg caatgaggtt 840
tggtggacca ttgatggaaa aaaacctgat gacatcacta ttgatgtcac cattaacgaa 900
agtataagtc atagtagaac agaagatgaa acaagaactc agattttgag catcaagaaa 960
gttacctctg aggatctcaa gcgcagctat gtctgtcatg ctagaagtgc caaaggcgaa 1020
gttgccaaag cagccaaggt gaagcagaaa gtgccagctc caagatacac agtggaaaaa 1080
tgcaaggaac gtgaagaaaa aataatttta gtgagctcag caaatgaaat cgatgttcgt 1140
ccctgtcctc ttaacccaaa tgaacacaaa ggcactataa cttggtataa ggatgacagc 1200
aagacacctg tatctacaga acaagcctcc aggattcatc aacacaaaga gaaactttgg 1260
tttgttcctg ctaaggtgga ggattcagga cattactatt gcgtggtaag aaattcatct 1320
tactgcctca gaattaaaat aagtgcaaaa tttgtggaga atgagcctaa cttatgttat 1380
aatgcacaag ccatatttaa gcagaaacta cccgttgcag gagacggagg acttgtgtgc 1440
ccttatatgg agttttttaa aaatgaaaat aatgagttac ctaaattaca gtggtataag 1500
gattgcaaac ctctacttct tgacaatata cactttagtg gagtcaaaga taggctcatc 1560
gtgatgaatg tggctgaaaa gcatagaggg aactatactt gtcatgcatc ctacacatac 1620
ttgggcaagc aatatcctat tacccgggta atagaattta ttactctaga ggaaaacaaa 1680
cccacaaggc ctgtgattgt gagcccagct aatgagacaa tggaagtaga cttgggatcc 1740
cagatacaat tgatctgtaa tgtcaccggc cagttgagtg acattgctta ctggaagtgg 1800
aatgggtcag taattgatga agatgaccca gtgctagggg aagactatta cagtgtggaa 1860
aatcctgcaa acaaaagaag gagtaccctc atcacagtgc ttaatatatc ggaaattgag 1920
agtagatttt ataaacatcc atttacctgt tttgccaaga atacacatgg tatagatgca 1980
gcatatatcc agttaatata tccagtcact aattccggag agtccaaata cggtccgcca 2040

-continued tgcccaccat gcccagcacc tgagttcctg gggggaccat cagtcttcct gttcccccca 2100
aaacccaagg acactctcat gatctcccgg acccctgagg tcacgtgcgt ggtggtggac 2160
gtgagccagg aagaccccga ggtccagttc aactggtacg tggatggcgt ggaggtgcat 2220
aatgccaaga caaagccgcg ggaggagcag ttcaacagca cgtaccgtgt ggtcagcgtc 2280
ctcaccgtcc tgcaccagga ctggctgaac ggcaaggagt acaagtgcaa ggtctccaac 2340
aaaggcctcc cgtcctccat cgagaaaacc atctccaaag ccaaagggca gccccgagag 2400
ccacaggtgt acaccctgcc cccatcccag gaggagatga ccaagaacca ggtcagcctg 2460
acctgcctgg tcaaaggctt ctaccccagc gacatcgccg tggagtggga gagcaatggg 2520
cagccggaga acaactacaa gaccacgcct cccgtgctgg actccgacgg ctccttcttc 2580
ctctacagca ggctaaccgt ggacaagagc aggtggcagg aggggaatgt cttctcatgc 2640
tccgtgatgc atgaggctct gcacaaccac tacacacaga agagcctctc cctgtctctg 2700
ggtaaatga 2709

<210> SEQ ID NO 14
<211> LENGTH: 902
<212> TYPE: PRT
<213> ORGANISM: Homo sapiens

<400> SEQUENCE: 14

Met Val Leu Leu Trp Cys Val Val Ser Leu Tyr Phe Tyr Gly Ile Leu
1 5 10 15

Gln Ser Asp Ala Ser Glu Arg Cys Asp Asp Trp Gly Leu Asp Thr Met
20 25 30

Arg Gln Ile Gln Val Phe Glu Asp Glu Pro Ala Arg Ile Lys Cys Pro
35 40 45

Leu Phe Glu His Phe Leu Lys Phe Asn Tyr Ser Thr Ala His Ser Ala
50 55 60

Gly Leu Thr Leu Ile Trp Tyr Trp Thr Arg Gln Asp Arg Asp Leu Glu
65 70 75 80

Glu Pro Ile Asn Phe Arg Leu Pro Glu Asn Arg Ile Ser Lys Glu Lys
85 90 95

Asp Val Leu Trp Phe Arg Pro Thr Leu Leu Asn Asp Thr Gly Asn Tyr
100 105 110

Thr Cys Met Leu Arg Asn Thr Thr Tyr Cys Ser Lys Val Ala Phe Pro
115 120 125

Leu Glu Val Val Gln Lys Asp Ser Cys Phe Asn Ser Pro Met Lys Leu
130 135 140

Pro Val His Lys Leu Tyr Ile Glu Tyr Gly Ile Gln Arg Ile Thr Cys
145 150 155 160

Pro Asn Val Asp Gly Tyr Phe Pro Ser Ser Val Lys Pro Thr Ile Thr
165 170 175

Trp Tyr Met Gly Cys Tyr Lys Ile Gln Asn Phe Asn Asn Val Ile Pro
180 185 190

Glu Gly Met Asn Leu Ser Phe Leu Ile Ala Leu Ile Ser Asn Asn Gly
195 200 205

Asn Tyr Thr Cys Val Val Thr Tyr Pro Glu Asn Gly Arg Thr Phe His
210 215 220

Leu Thr Arg Thr Leu Thr Val Lys Val Val Gly Ser Pro Lys Asn Ala
225 230 235 240

Val Pro Pro Val Ile His Ser Pro Asn Asp His Val Val Tyr Glu Lys

-continued

```
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Glu Lys Ile
        355                 360                 365

Ile Leu Val Ser Ser Ala Asn Glu Ile Asp Val Arg Pro Cys Pro Leu
    370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
        435                 440                 445

Ala Lys Phe Val Glu Asn Glu Pro Asn Leu Cys Tyr Asn Ala Gln Ala
    450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
        515                 520                 525

Arg Gly Asn Tyr Thr Cys His Ala Ser Tyr Thr Tyr Leu Gly Lys Gln
    530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
        595                 600                 605

Asp Pro Val Leu Gly Glu Asp Tyr Tyr Ser Val Glu Asn Pro Ala Asn
    610                 615                 620

Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
                645                 650                 655

Gly Ile Asp Ala Ala Tyr Ile Gln Leu Ile Tyr Pro Val Thr Asn Ser
            660                 665                 670
```

-continued

```
Gly Glu Ser Lys Tyr Gly Pro Pro Cys Pro Pro Cys Pro Ala Pro Glu
        675                 680                 685

Phe Leu Gly Gly Pro Ser Val Phe Leu Phe Pro Pro Lys Pro Lys Asp
    690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
            740                 745                 750

Ser Thr Tyr Arg Val Val Ser Val Leu Thr Val Leu His Gln Asp Trp
        755                 760                 765

Leu Asn Gly Lys Glu Tyr Lys Cys Lys Val Ser Asn Lys Gly Leu Pro
    770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
                805                 810                 815

Gln Val Ser Leu Thr Cys Leu Val Lys Gly Phe Tyr Pro Ser Asp Ile
            820                 825                 830

Ala Val Glu Trp Glu Ser Asn Gly Gln Pro Glu Asn Asn Tyr Lys Thr
        835                 840                 845

Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900


<210> SEQ ID NO 15
<211> LENGTH: 2748
<212> TYPE: DNA
<213> ORGANISM: Homo sapiens

<400> SEQUENCE: 15

atggtgcgct tgtacgtgtt ggtaatggga gtttctgcct tcacccttca gcctgcggca      60

cacacagggg ctgccagaag ctgccggttt cgtgggaggc attacaagcg ggagttcagg     120

ctggaagggg agcctgtagc cctgaggtgc ccccaggtgc cctactggtt gtgggcctct     180

gtcagccccc gcatcaacct gacatggcat aaaaatgact ctgctaggac ggtcccagga     240

gaagaagaga cacggatgtg ggcccaggac ggtgctctgt ggcttctgcc agccttgcag     300

gaggactctg gcacctacgt ctgcactact agaaatgctt cttactgtga caaaatgtcc     360

attgagctca gagtttttga gaatacagat gctttcctgc cgttcatctc atacccgcaa     420

attttaacct tgtcaacctc tggggtatta gtatgccctg acctgagtga attcacccgt     480

gacaaaactg acgtgaagat tcaatggtac aaggattctc ttcttttgga taaagacaat     540

gagaaatttc taagtgtgag ggggaccact cacttactcg tacacgatgt ggccctggaa     600

gatgctggct attaccgctg tgtcctgaca tttgcccatg aaggccagca atacaacatc     660

actaggagta ttgagctacg catcaagaaa aaaaaagaag agaccattcc tgtgatcatt     720

tccccccctca agaccatatc agcttctctg ggtcaagac tgacaatccc atgtaaggtg     780
```

-continued

```
tttctgggaa ccggcacacc cttaaccacc atgctgtggt ggacggccaa tgacacccac    840
atagagagcg cctacccggg aggccgcgtg accgaggggc cacgccagga atattcagaa    900
aataatgaga actacattga agtgccattg atttttgatc ctgtcacaag agaggatttg    960
cacatggatt ttaaatgtgt tgtccataat accctgagtt ttcagacact acgcaccaca   1020
gtcaaggaag cctcctccac gttctcagaa cgctgcgatg actggggact agacaccatg   1080
aggcaaatcc aagtgtttga agatgagcca gctcgcatca agtgcccact ctttgaacac   1140
ttcttgaaat tcaactacag cacagcccat tcagctggcc ttactctgat ctggtattgg   1200
actaggcagg accgggacct tgaggagcca attaacttcc gcctccccga gaaccgcatt   1260
agtaaggaga aagatgtgct gtggttccgg cccactctcc tcaatgacac tggcaactat   1320
acctgcatgt taaggaacac tacatattgc agcaaagttg catttccctt ggaagttgtt   1380
caaaaagaca gctgtttcaa ttcccccatg aaactcccag tgcataaact gtatatagaa   1440
tatggcattc agaggatcac ttgtccaaat gtagatggat attttccttc cagtgtcaaa   1500
ccgactatca cttggtatat gggctgttat aaaatacaga attttaataa tgtaataccc   1560
gaaggtatga acttgagttt cctcattgcc ttaatttcaa ataatggaaa ttacacatgt   1620
gttgttacat atccagaaaa tggacgtacg tttcatctca ccaggactct gactgtaaag   1680
gtagtaggct ctccaaaaaa tgcagtgccc cctgtgatcc attcacctaa tgatcatgtg   1740
gtctatgaga aagaaccagg agaggagcta ctcattccct gtacggtcta ttttagtttt   1800
ctgatggatt ctcgcaatga ggtttggtgg accattgatg gaaaaaaacc tgatgacatc   1860
actattgatg tcaccattaa cgaaagtata agtcatagta gaacagaaga tgaaacaaga   1920
actcagattt tgagcatcaa gaaagttacc tctgaggatc tcaagcgcag ctatgtctgt   1980
catgctagaa gtgccaaagg cgaagttgcc aaagcagcca aggtgaagca gaaagtgcca   2040
gctccaagat acacagtgtc cggagacaaa actcacacat gcccaccgtg cccagcacct   2100
gaactcctgg ggggaccgtc agtcttcctc ttccccccaa aacccaagga caccctcatg   2160
atctcccgga cccctgaggt cacatgcgtg gtggtggacg tgagccacga agaccctgag   2220
gtcaagttca actggtacgt ggacggcgtg gaggtgcata atgccaagac aaagccgcgg   2280
gaggagcagt acaacagcac gtaccgtgtg gtcagcgtcc tcaccgtcct gcaccaggac   2340
tggctgaatg gcaaggagta caagtgcaag gtctccaaca aagccctccc agcccccatc   2400
gagaaaacca tctccaaagc caaagggcag ccccgagaac cacaggtgta caccctgccc   2460
ccatcccggg atgagctgac caagaaccag gtcagcctga cctgcctggt caaaggcttc   2520
tatcccagcg acatcgccgt ggagtgggag agcaatgggc agccggagaa caactacaag   2580
accacgcctc ccgtgctgga ctccgacggc tccttcttcc tctatagcaa gctcaccgtg   2640
gacaagagca ggtggcagca ggggaacgtc ttctcatgct ccgtgatgca tgaggctctg   2700
cacaaccact acacgcagaa gagcctctcc ctgtctccgg gtaaatga                2748
```

<210> SEQ ID NO 16
<211> LENGTH: 915
<212> TYPE: PRT
<213> ORGANISM: Homo sapiens

<400> SEQUENCE: 16

```
Met Val Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
```

-continued

```
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445
```

-continued

```
Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Asp Lys Thr His Thr Cys Pro Pro Cys Pro Ala Pro Glu Leu Leu Gly
    690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
                725                 730                 735

Glu Asp Pro Glu Val Lys Phe Asn Trp Tyr Val Asp Gly Val Glu Val
            740                 745                 750

His Asn Ala Lys Thr Lys Pro Arg Glu Glu Gln Tyr Asn Ser Thr Tyr
        755                 760                 765

Arg Val Val Ser Val Leu Thr Val Leu His Gln Asp Trp Leu Asn Gly
    770                 775                 780

Lys Glu Tyr Lys Cys Lys Val Ser Asn Lys Ala Leu Pro Ala Pro Ile
785                 790                 795                 800

Glu Lys Thr Ile Ser Lys Ala Lys Gly Gln Pro Arg Glu Pro Gln Val
                805                 810                 815

Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
    850                 855                 860
```

-continued

```
Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
        915


<210> SEQ ID NO 17
<211> LENGTH: 2754
<212> TYPE: DNA
<213> ORGANISM: Homo sapiens

<400> SEQUENCE: 17

atggtgcgct tgtacgtgtt ggtaatggga gtttctgcct tcacccttca gcctgcggca      60

cacacagggg ctgccagaag ctgccggttt cgtgggaggc attacaagcg ggagttcagg     120

ctggaagggg agcctgtagc cctgaggtgc ccccaggtgc cctactggtt gtgggcctct     180

gtcagccccc gcatcaacct gacatggcat aaaaatgact ctgctaggac ggtcccagga     240

gaagaagaga cacggatgtg ggcccaggac ggtgctctgt ggcttctgcc agccttgcag     300

gaggactctg gcacctacgt ctgcactact agaaatgctt cttactgtga caaaatgtcc     360

attgagctca gagtttttga gaatacagat gctttcctgc cgttcatctc atacccgcaa     420

attttaacct tgtcaacctc tggggtatta gtatgccctg acctgagtga attcacccgt     480

gacaaaactg acgtgaagat tcaatggtac aaggattctc ttcttttgga taaagacaat     540

gagaaatttc taagtgtgag gggaccact cacttactcg tacacgatgt ggccctggaa     600

gatgctggct attaccgctg tgtcctgaca tttgcccatg aaggccagca atacaacatc     660

actaggagta ttgagctacg catcaagaaa aaaaaagaag agaccattcc tgtgatcatt     720

tccccctca agaccatatc agcttctctg gggtcaagac tgacaatccc atgtaaggtg     780

tttctgggaa ccggcacacc cttaaccacc atgctgtggt ggacggccaa tgacacccac     840

atagagagcg cctacccggg aggccgcgtg accgaggggc cacgccagga atattcagaa     900

aataatgaga actacattga agtgccattg atttttgatc ctgtcacaag agaggatttg     960

cacatggatt ttaaatgtgt tgtccataat accctgagtt ttcagacact acgcaccaca    1020

gtcaaggaag cctcctccac gttctcagaa cgctgcgatg actggggact agacaccatg    1080

aggcaaatcc aagtgtttga agatgagcca gctcgcatca agtgcccact ctttgaacac    1140

ttcttgaaat tcaactacag cacagcccat tcagctggcc ttactctgat ctggtattgg    1200

actaggcagg accgggacct tgaggagcca attaacttcc gcctccccga gaaccgcatt    1260

agtaaggaga aagatgtgct gtggttccgg cccactctcc tcaatgacac tggcaactat    1320

acctgcatgt taaggaacac tacatattgc agcaaagttg catttccctt ggaagttgtt    1380

caaaaagaca gctgtttcaa ttcccccatg aaactcccag tgcataaact gtatatagaa    1440

tatggcattc agaggatcac ttgtccaaat gtagatggat attttccttc cagtgtcaaa    1500

ccgactatca cttggtatat gggctgttat aaaatacaga attttaataa tgtaataccc    1560

gaaggtatga acttgagttt cctcattgcc ttaatttcaa ataatggaaa ttacacatgt    1620

gttgttacat atccagaaaa tggacgtacg tttcatctca ccaggactct gactgtaaag    1680

gtagtaggct ctccaaaaaa tgcagtgccc cctgtgatcc attcacctaa tgatcatgtg    1740

gtctatgaga aagaaccagg agaggagcta ctcattccct gtacggtcta ttttagtttt    1800
```

-continued

```
ctgatggatt ctcgcaatga ggtttggtgg accattgatg gaaaaaaacc tgatgacatc   1860

actattgatg tcaccattaa cgaaagtata agtcatagta gaacagaaga tgaaacaaga   1920

actcagattt tgagcatcaa gaaagttacc tctgaggatc tcaagcgcag ctatgtctgt   1980

catgctagaa gtgccaaagg cgaagttgcc aaagcagcca aggtgaagca gaaagtgcca   2040

gctccaagat acacagtgtc cggagagtcc aaatacggtc cgccatgccc atcatgccca   2100

gcacctgagt tcctgggggg accatcagtc ttcctgttcc ccccaaaacc caaggacact   2160

ctcatgatct cccggacccc tgaggtcacg tgcgtggtgg tggacgtgag ccaggaagac   2220

cccgaggtcc agttcaactg gtacgtggat ggcgtggagg tgcataatgc caagacaaag   2280

ccgcgggagg agcagttcaa cagcacgtac cgtgtggtca gcgtcctcac cgtcctgcac   2340

caggactggc tgaacggcaa ggagtacaag tgcaaggtct ccaacaaagg cctcccgtcc   2400

tccatcgaga aaaccatctc caaagccaaa gggcagcccc gagagccaca ggtgtacacc   2460

ctgcccccat cccaggagga gatgaccaag aaccaggtca gcctgacctg cctggtcaaa   2520

ggcttctacc ccagcgacat cgccgtggag tgggagagca atgggcagcc ggagaacaac   2580

tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga         2754
```

```
<210> SEQ ID NO 18
<211> LENGTH: 917
<212> TYPE: PRT
<213> ORGANISM: Homo sapiens

<400> SEQUENCE: 18

Met Val Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205
```

-continued

```
Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
    610                 615                 620
```

-continued

Thr Ile Asn Glu Ser Ile Ser His Ser Arg Thr Glu Asp Glu Thr Arg
625 630 635 640

Thr Gln Ile Leu Ser Ile Lys Lys Val Thr Ser Glu Asp Leu Lys Arg
645 650 655

Ser Tyr Val Cys His Ala Arg Ser Ala Lys Gly Glu Val Ala Lys Ala
660 665 670

Ala Lys Val Lys Gln Lys Val Pro Ala Pro Arg Tyr Thr Val Ser Gly
675 680 685

Glu Ser Lys Tyr Gly Pro Pro Cys Pro Ser Cys Pro Ala Pro Glu Phe
690 695 700

Leu Gly Gly Pro Ser Val Phe Leu Phe Pro Pro Lys Pro Lys Asp Thr
705 710 715 720

Leu Met Ile Ser Arg Thr Pro Glu Val Thr Cys Val Val Val Asp Val
725 730 735

Ser Gln Glu Asp Pro Glu Val Gln Phe Asn Trp Tyr Val Asp Gly Val
740 745 750

Glu Val His Asn Ala Lys Thr Lys Pro Arg Glu Glu Gln Phe Asn Ser
755 760 765

Thr Tyr Arg Val Val Ser Val Leu Thr Val Leu His Gln Asp Trp Leu
770 775 780

Asn Gly Lys Glu Tyr Lys Cys Lys Val Ser Asn Lys Gly Leu Pro Ser
785 790 795 800

Ser Ile Glu Lys Thr Ile Ser Lys Ala Lys Gly Gln Pro Arg Glu Pro
805 810 815

Gln Val Tyr Thr Leu Pro Pro Ser Gln Glu Glu Met Thr Lys Asn Gln
820 825 830

Val Ser Leu Thr Cys Leu Val Lys Gly Phe Tyr Pro Ser Asp Ile Ala
835 840 845

Val Glu Trp Glu Ser Asn Gly Gln Pro Glu Asn Asn Tyr Lys Thr Thr
850 855 860

Pro Pro Val Leu Asp Ser Asp Gly Ser Phe Phe Leu Tyr Ser Arg Leu
865 870 875 880

Thr Val Asp Lys Ser Arg Trp Gln Glu Gly Asn Val Phe Ser Cys Ser
885 890 895

Val Met His Glu Ala Leu His Asn His Tyr Thr Gln Lys Ser Leu Ser
900 905 910

Leu Ser Leu Gly Lys
915

<210> SEQ ID NO 19
<211> LENGTH: 2754
<212> TYPE: DNA
<213> ORGANISM: Homo sapiens

<400> SEQUENCE: 19
atggtgcgct tgtacgtgtt ggtaatggga gtttctgcct tcacccttca gcctgcggca 60
cacacagggg ctgccagaag ctgccggttt cgtgggaggc attacaagcg ggagttcagg 120
ctggaagggg agcctgtagc cctgaggtgc ccccaggtgc cctactggtt gtgggcctct 180
gtcagccccc gcatcaacct gacatggcat aaaaatgact ctgctaggac ggtcccagga 240
gaagaagaga cacggatgtg ggcccaggac ggtgctctgt ggcttctgcc agccttgcag 300
gaggactctg gcacctacgt ctgcactact agaaatgctt cttactgtga caaaatgtcc 360
attgagctca gagtttttga gaatacagat gctttcctgc cgttcatctc atacccgcaa 420

-continued

```
atttttaacct tgtcaacctc tggggtatta gtatgccctg acctgagtga attcacccgt    480
```

```
gacaaaactg acgtgaagat tcaatggtac aaggattctc ttcttttgga taaagacaat    540

gagaaatttc taagtgtgag gggaccact cacttactcg tacacgatgt ggccctggaa    600

gatgctggct attaccgctg tgtcctgaca tttgcccatg aaggccagca atacaacatc    660

actaggagta ttgagctacg catcaagaaa aaaaaagaag agaccattcc tgtgatcatt    720

tccccccctca agaccatatc agcttctctg ggtcaagac tgacaatccc atgtaaggtg    780

tttctgggaa ccggcacacc cttaaccacc atgctgtggt ggacggccaa tgacacccac    840

atagagagcg cctacccggg aggccgcgtg accgaggggc cacgccagga atattcagaa    900

aataatgaga actacattga agtgccattg atttttgatc ctgtcacaag agaggatttg    960

cacatggatt ttaaatgtgt tgtccataat accctgagtt ttcagacact acgcaccaca   1020

gtcaaggaag cctcctccac gttctcagaa cgctgcgatg actggggact agacaccatg   1080

aggcaaatcc aagtgtttga agatgagcca gctcgcatca agtgcccact ctttgaacac   1140

ttcttgaaat tcaactacag cacagcccat tcagctggcc ttactctgat ctggtattgg   1200

actaggcagg accgggacct tgaggagcca attaacttcc gcctccccga gaaccgcatt   1260

agtaaggaga aagatgtgct gtggttccgg cccactctcc tcaatgacac tggcaactat   1320

acctgcatgt taaggaacac tacatattgc agcaaagttg catttccctt ggaagttgtt   1380

caaaaagaca gctgtttcaa ttccccccatg aaactcccag tgcataaact gtatatagaa   1440

tatggcattc agaggatcac ttgtccaaat gtagatggat attttccttc cagtgtcaaa   1500

ccgactatca cttggtatat gggctgttat aaaatacaga attttaataa tgtaataccc   1560

gaaggtatga acttgagttt cctcattgcc ttaatttcaa ataatggaaa ttacacatgt   1620

gttgttacat atccagaaaa tggacgtacg tttcatctca ccaggactct gactgtaaag   1680

gtagtaggct ctccaaaaaa tgcagtgccc cctgtgatcc attcacctaa tgatcatgtg   1740

gtctatgaga aagaaccagg agaggagcta ctcattccct gtacggtcta ttttagtttt   1800

ctgatggatt ctcgcaatga ggtttggtgg accattgatg gaaaaaaacc tgatgacatc   1860

actattgatg tcaccattaa cgaaagtata agtcatagta gaacagaaga tgaaacaaga   1920

actcagattt tgagcatcaa gaaagttacc tctgaggatc tcaagcgcag ctatgtctgt   1980

catgctagaa gtgccaaagg cgaagttgcc aaagcagcca aggtgaagca gaaagtgcca   2040

gctccaagat acacagtgtc cggagagtcc aaatacggtc cgccatgccc accatgccca   2100

gcacctgagt tcctgggggg accatcagtc ttcctgttcc ccccaaaacc caaggacact   2160

ctcatgatct cccggacccc tgaggtcacg tgcgtggtgg tggacgtgag ccaggaagac   2220

cccgaggtcc agttcaactg gtacgtggat ggcgtggagg tgcataatgc caagacaaag   2280

ccgcgggagg agcagttcaa cagcacgtac cgtgtggtca gcgtcctcac cgtcctgcac   2340

caggactggc tgaacggcaa ggagtacaag tgcaaggtct ccaacaaagg cctcccgtcc   2400

tccatcgaga aaaccatctc caaagccaaa gggcagcccc gagagccaca ggtgtacacc   2460

ctgcccccat cccaggagga gatgaccaag aaccaggtca gcctgacctg cctggtcaaa   2520

ggcttctacc ccagcgacat cgccgtggag tgggagagca atgggcagcc ggagaacaac   2580

tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga         2754
```

-continued

<210> SEQ ID NO 20
<211> LENGTH: 917
<212> TYPE: PRT
<213> ORGANISM: Homo sapiens

<400> SEQUENCE: 20

```
Met Val Arg Leu Tyr Val Leu Val Met Gly Val Ser Ala Phe Thr Leu
 1               5                  10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
            340                 345                 350

Asp Asp Trp Gly Leu Asp Thr Met Arg Gln Ile Gln Val Phe Glu Asp
        355                 360                 365

Glu Pro Ala Arg Ile Lys Cys Pro Leu Phe Glu His Phe Leu Lys Phe
    370                 375                 380
```

-continued

```
Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                405                 410                 415

Glu Asn Arg Ile Ser Lys Glu Lys Asp Val Leu Trp Phe Arg Pro Thr
            420                 425                 430

Leu Leu Asn Asp Thr Gly Asn Tyr Thr Cys Met Leu Arg Asn Thr Thr
        435                 440                 445

Tyr Cys Ser Lys Val Ala Phe Pro Leu Glu Val Val Gln Lys Asp Ser
    450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                485                 490                 495

Ser Ser Val Lys Pro Thr Ile Thr Trp Tyr Met Gly Cys Tyr Lys Ile
            500                 505                 510

Gln Asn Phe Asn Asn Val Ile Pro Glu Gly Met Asn Leu Ser Phe Leu
        515                 520                 525

Ile Ala Leu Ile Ser Asn Asn Gly Asn Tyr Thr Cys Val Val Thr Tyr
    530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                565                 570                 575

Asn Asp His Val Val Tyr Glu Lys Glu Pro Gly Glu Glu Leu Leu Ile
            580                 585                 590

Pro Cys Thr Val Tyr Phe Ser Phe Leu Met Asp Ser Arg Asn Glu Val
        595                 600                 605

Trp Trp Thr Ile Asp Gly Lys Lys Pro Asp Asp Ile Thr Ile Asp Val
    610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                645                 650                 655

Ser Tyr Val Cys His Ala Arg Ser Ala Lys Gly Glu Val Ala Lys Ala
            660                 665                 670

Ala Lys Val Lys Gln Lys Val Pro Ala Pro Arg Tyr Thr Val Ser Gly
        675                 680                 685

Glu Ser Lys Tyr Gly Pro Pro Cys Pro Pro Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
```

-continued

```
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915


<210> SEQ ID NO 21
<211> LENGTH: 2748
<212> TYPE: DNA
<213> ORGANISM: Homo sapiens

<400> SEQUENCE: 21

atggtgcttc tgtggtgtgt agtgagtctc tacttttatg gaatcctgca aagtgatgcc      60

tcagaacgct gcgatgactg gggactagac accatgaggc aaatccaagt gtttgaagat     120

gagccagctc gcatcaagtg cccactcttt gaacacttct tgaaattcaa ctacagcaca     180

gcccattcag ctggccttac tctgatctgg tattggacta ggcaggaccg ggaccttgag     240

gagccaatta acttccgcct ccccgagaac cgcattagta aggagaaaga tgtgctgtgg     300

ttccggccca ctctcctcaa tgacactggc aactatacct gcatgttaag gaacactaca     360

tattgcagca aagttgcatt tcccttggaa gttgttcaaa aagacagctg tttcaattcc     420

cccatgaaac tcccagtgca taaactgtat atagaatatg gcattcagag gatcacttgt     480

ccaaatgtag atggatattt tccttccagt gtcaaaccga ctatcacttg gtatatgggc     540

tgttataaaa tacagaattt taataatgta atacccgaag gtatgaactt gagtttcctc     600

attgccttaa tttcaaataa tggaaattac acatgtgttg ttacatatcc agaaaatgga     660

cgtacgtttc atctcaccag gactctgact gtaaaggtag taggctctcc aaaaaatgca     720

gtgccccctg tgatccattc acctaatgat catgtggtct atgagaaaga accaggagag     780

gagctactca ttccctgtac ggtctatttt agttttctga tggattctcg caatgaggtt     840

tggtggacca ttgatggaaa aaaacctgat gacatcacta ttgatgtcac cattaacgaa     900

agtataagtc atagtagaac agaagatgaa acaagaactc agattttgag catcaagaaa     960

gttacctctg aggatctcaa gcgcagctat gtctgtcatg ctagaagtgc caaaggcgaa    1020

gttgccaaag cagccaaggt gaagcagaaa gtgccagctc caagatacac agtgcacaca    1080

ggggctgcca gaagctgccg gtttcgtggg aggcattaca agcgggagtt caggctggaa    1140

ggggagcctg tagccctgag gtgcccccag gtgccctact ggttgtgggc ctctgtcagc    1200

ccccgcatca acctgacatg gcataaaaat gactctgcta ggacggtccc aggagaagaa    1260

gagacacgga tgtgggccca ggacggtgct ctgtggcttc tgccagcctt gcaggaggac    1320

tctggcacct acgtctgcac tactagaaat gcttcttact gtgacaaaat gtccattgag    1380

ctcagagttt ttgagaatac agatgctttc ctgccgttca tctcataccc gcaaatttta    1440
```

-continued

```
accttgtcaa cctctggggt attagtatgc cctgacctga gtgaattcac ccgtgacaaa   1500

actgacgtga agattcaatg gtacaaggat tctcttcttt tggataaaga caatgagaaa   1560

tttctaagtg tgagggggac cactcactta ctcgtacacg atgtggccct ggaagatgct   1620

ggctattacc gctgtgtcct gacatttgcc catgaaggcc agcaatacaa catcactagg   1680

agtattgagc tacgcatcaa gaaaaaaaaa gaagagacca ttcctgtgat catttccccc   1740

ctcaagacca tatcagcttc tctggggtca agactgacaa tcccatgtaa ggtgtttctg   1800

ggaaccggca cacccttaac caccatgctg tggtggacgg ccaatgacac ccacatagag   1860

agcgcctacc cgggaggccg cgtgaccgag gggccacgcc aggaatattc agaaaataat   1920

gagaactaca ttgaagtgcc attgattttt gatcctgtca caagagagga tttgcacatg   1980

gattttaaat gtgttgtcca taataccctg agttttcaga cactacgcac cacagtcaag   2040

gaagcctcct ccacgttctc cggagacaaa actcacacat gcccaccgtg cccagcacct   2100

gaactcctgg ggggaccgtc agtcttcctc ttccccccaa aacccaagga caccctcatg   2160

atctcccgga cccctgaggt cacatgcgtg gtggtggacg tgagccacga agaccctgag   2220

gtcaagttca actggtacgt ggacggcgtg gaggtgcata atgccaagac aaagccgcgg   2280

gaggagcagt acaacagcac gtaccgtgtg gtcagcgtcc tcaccgtcct gcaccaggac   2340

tggctgaatg gcaaggagta caagtgcaag gtctccaaca aagccctccc agcccccatc   2400

gagaaaacca tctccaaagc caaagggcag ccccgagaac cacaggtgta caccctgccc   2460

ccatcccggg atgagctgac caagaaccag gtcagcctga cctgcctggt caaaggcttc   2520

tatcccagcg acatcgccgt ggagtgggag agcaatgggc agccggagaa caactacaag   2580

accacgcctc ccgtgctgga ctccgacggc tccttcttcc tctatagcaa gctcaccgtg   2640

gacaagagca ggtggcagca ggggaacgtc ttctcatgct ccgtgatgca tgaggctctg   2700

cacaaccact acacgcagaa gagcctctcc ctgtctccgg gtaaatga                 2748
```

```
<210> SEQ ID NO 22
<211> LENGTH: 915
<212> TYPE: PRT
<213> ORGANISM: Homo sapiens

<400> SEQUENCE: 22

Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140
```

-continued

```
Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
```

```
                        565                 570                 575
Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
            595                 600                 605

Met Leu Trp Trp Thr Ala Asn Asp Thr His Ile Glu Ser Ala Tyr Pro
            610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Asp Lys Thr His Thr Cys Pro Pro Cys Pro Ala Pro Glu Leu Leu Gly
    690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
                725                 730                 735

Glu Asp Pro Glu Val Lys Phe Asn Trp Tyr Val Asp Gly Val Glu Val
            740                 745                 750

His Asn Ala Lys Thr Lys Pro Arg Glu Glu Gln Tyr Asn Ser Thr Tyr
        755                 760                 765

Arg Val Val Ser Val Leu Thr Val Leu His Gln Asp Trp Leu Asn Gly
    770                 775                 780

Lys Glu Tyr Lys Cys Lys Val Ser Asn Lys Ala Leu Pro Ala Pro Ile
785                 790                 795                 800

Glu Lys Thr Ile Ser Lys Ala Lys Gly Gln Pro Arg Glu Pro Gln Val
                805                 810                 815

Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
    850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
        915

<210> SEQ ID NO 23
<211> LENGTH: 2754
<212> TYPE: DNA
<213> ORGANISM: Homo sapiens

<400> SEQUENCE: 23

atggtgcttc tgtggtgtgt agtgagtctc tacttttatg gaatcctgca aagtgatgcc      60

tcagaacgct gcgatgactg gggactagac accatgaggc aaatccaagt gtttgaagat     120
```

-continued

```
gagccagctc gcatcaagtg cccactcttt gaacacttct tgaaattcaa ctacagcaca    180
gcccattcag ctggccttac tctgatctgg tattggacta ggcaggaccg ggaccttgag    240
gagccaatta acttccgcct ccccgagaac cgcattagta aggagaaaga tgtgctgtgg    300
ttccggccca ctctcctcaa tgacactggc aactatacct gcatgttaag gaacactaca    360
tattgcagca aagttgcatt tcccttggaa gttgttcaaa aagacagctg tttcaattcc    420
cccatgaaac tcccagtgca taaactgtat atagaatatg gcattcagag gatcacttgt    480
ccaaatgtag atggatattt tccttccagt gtcaaaccga ctatcacttg gtatatgggc    540
tgttataaaa tacagaattt taataatgta atacccgaag gtatgaactt gagtttcctc    600
attgccttaa tttcaaataa tggaaattac acatgtgttg ttacatatcc agaaaatgga    660
cgtacgtttc atctcaccag gactctgact gtaaaggtag taggctctcc aaaaaatgca    720
gtgccccctg tgatccattc acctaatgat catgtggtct atgagaaaga accaggagag    780
gagctactca ttccctgtac ggtctatttt agttttctga tggattctcg caatgaggtt    840
tggtggacca ttgatggaaa aaaacctgat gacatcacta ttgatgtcac cattaacgaa    900
agtataagtc atagtagaac agaagatgaa acaagaactc agattttgag catcaagaaa    960
gttacctctg aggatctcaa gcgcagctat gtctgtcatg ctagaagtgc caaaggcgaa   1020
gttgccaaag cagccaaggt gaagcagaaa gtgccagctc caagatacac agtgcacaca   1080
ggggctgcca gaagctgccg gtttcgtggg aggcattaca agcgggagtt caggctggaa   1140
ggggagcctg tagccctgag gtgcccccag gtgccctact ggttgtgggc ctctgtcagc   1200
ccccgcatca acctgacatg gcataaaaat gactctgcta ggacggtccc aggagaagaa   1260
gagacacgga tgtgggccca ggacggtgct ctgtggcttc tgccagcctt gcaggaggac   1320
tctggcacct acgtctgcac tactagaaat gcttcttact gtgacaaaat gtccattgag   1380
ctcagagttt ttgagaatac agatgctttc ctgccgttca tctcataccc gcaaatttta   1440
accttgtcaa cctctggggt attagtatgc cctgacctga gtgaattcac ccgtgacaaa   1500
actgacgtga agattcaatg gtacaaggat tctcttcttt tggataaaga caatgagaaa   1560
tttctaagtg tgagggggac cactcactta ctcgtacacg atgtggccct ggaagatgct   1620
ggctattacc gctgtgtcct gacatttgcc catgaaggcc agcaatacaa catcactagg   1680
agtattgagc tacgcatcaa gaaaaaaaaa gaagagacca ttcctgtgat catttccccc   1740
ctcaagacca tatcagcttc tctggggtca agactgacaa tcccatgtaa ggtgtttctg   1800
ggaaccggca caccccttaac caccatgctg tggtggacgg ccaatgacac ccacatagag   1860
agcgcctacc cgggaggccg cgtgaccgag gggccacgcc aggaatattc agaaaataat   1920
gagaactaca ttgaagtgcc attgattttt gatcctgtca caagagagga tttgcacatg   1980
gattttaaat gtgttgtcca taataccctg agttttcaga cactacgcac cacagtcaag   2040
gaagcctcct ccacgttctc cggagagtcc aaatacggtc cgccatgccc atcatgccca   2100
gcacctgagt tcctgggggg accatcagtc ttcctgttcc ccccaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460
```

-continued

```
ctgcccccat cccaggagga gatgaccaag aaccaggtca gcctgacctg cctggtcaaa   2520

ggcttctacc ccagcgacat cgccgtggag tgggagagca atgggcagcc ggagaacaac   2580

tacaagacca cgcctcccgt gctggactcc gacggctcct tcttcctcta cagcaggcta   2640

accgtggaca agagcaggtg gcaggagggg aatgtcttct catgctccgt gatgcatgag   2700

gctctgcaca accactacac acagaagagc ctctccctgt ctctgggtaa atga         2754


<210> SEQ ID NO 24
<211> LENGTH: 917
<212> TYPE: PRT
<213> ORGANISM: Homo sapiens

<400> SEQUENCE: 24

Met Val Leu Leu Trp Cys Val Val Ser Leu Tyr Phe Tyr Gly Ile Leu
1               5                   10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
```

-continued

```
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Glu Ser Lys Tyr Gly Pro Pro Cys Pro Ser Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750
```

-continued

```
Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915

<210> SEQ ID NO 25
<211> LENGTH: 2754
<212> TYPE: DNA
<213> ORGANISM: Homo sapiens

<400> SEQUENCE: 25

atggtgcttc tgtggtgtgt agtgagtctc tacttttatg gaatcctgca aagtgatgcc     60

tcagaacgct gcgatgactg ggactagac accatgaggc aaatccaagt gtttgaagat    120

gagccagctc gcatcaagtg cccactcttt gaacacttct tgaaattcaa ctacagcaca    180

gcccattcag ctggccttac tctgatctgg tattggacta ggcaggaccg ggaccttgag    240

gagccaatta acttccgcct ccccgagaac cgcattagta aggagaaaga tgtgctgtgg    300

ttccggccca ctctcctcaa tgacactggc aactatacct gcatgttaag gaacactaca    360

tattgcagca aagttgcatt tcccttggaa gttgttcaaa aagacagctg tttcaattcc    420

cccatgaaac tcccagtgca taaactgtat atagaatatg gcattcagag gatcacttgt    480

ccaaatgtag atggatattt tccttccagt gtcaaaccga ctatcacttg gtatatgggc    540

tgttataaaa tacagaattt taataatgta atacccgaag gtatgaactt gagtttcctc    600

attgccttaa tttcaaataa tggaaattac acatgtgttg ttacatatcc agaaaatgga    660

cgtacgtttc atctcaccag gactctgact gtaaaggtag taggctctcc aaaaaatgca    720

gtgccccctg tgatccattc acctaatgat catgtggtct atgagaaaga accaggagag    780

gagctactca ttccctgtac ggtctatttt agttttctga tggattctcg caatgaggtt    840

tggtggacca ttgatggaaa aaaacctgat gacatcacta ttgatgtcac cattaacgaa    900

agtataagtc atagtagaac agaagatgaa acaagaactc agattttgag catcaagaaa    960

gttacctctg aggatctcaa gcgcagctat gtctgtcatg ctagaagtgc caaaggcgaa   1020

gttgccaaag cagccaaggt gaagcagaaa gtgccagctc caagatacac agtgcacaca   1080

ggggctgcca gaagctgccg gtttcgtggg aggcattaca agcgggagtt caggctggaa   1140
```

-continued ggggagcctg tagccctgag gtgcccccag gtgccctact ggttgtgggc ctctgtcagc 1200
ccccgcatca acctgacatg gcataaaaat gactctgcta ggacggtccc aggagaagaa 1260
gagacacgga tgtgggccca ggacggtgct ctgtggcttc tgccagcctt gcaggaggac 1320
tctggcacct acgtctgcac tactagaaat gcttcttact gtgacaaaat gtccattgag 1380
ctcagagttt ttgagaatac agatgctttc ctgccgttca tctcataccc gcaaatttta 1440
accttgtcaa cctctggggt attagtatgc cctgacctga gtgaattcac ccgtgacaaa 1500
actgacgtga agattcaatg gtacaaggat tctcttcttt tggataaaga caatgagaaa 1560
tttctaagtg tgagggggac cactcactta ctcgtacacg atgtggccct ggaagatgct 1620
ggctattacc gctgtgtcct gacatttgcc catgaaggcc agcaatacaa catcactagg 1680
agtattgagc tacgcatcaa gaaaaaaaaa gaagagacca ttcctgtgat catttccccc 1740
ctcaagacca tatcagcttc tctggggtca agactgacaa tcccatgtaa ggtgtttctg 1800
ggaaccggca caccccttaac caccatgctg tggtggacgg ccaatgacac ccacatagag 1860
agcgcctacc cgggaggccg cgtgaccgag gggccacgcc aggaatattc agaaaataat 1920
gagaactaca ttgaagtgcc attgattttt gatcctgtca caagagagga tttgcacatg 1980
gattttaaat gtgttgtcca taataccctg agttttcaga cactacgcac cacagtcaag 2040
gaagcctcct ccacgttctc cggagagtcc aaatacggtc cgccatgccc accatgccca 2100
gcacctgagt tcctgggggg accatcagtc ttcctgttcc ccccaaaacc caaggacact 2160
ctcatgatct cccggacccc tgaggtcacg tgcgtggtgg tggacgtgag ccaggaagac 2220
cccgaggtcc agttcaactg gtacgtggat ggcgtggagg tgcataatgc caagacaaag 2280
ccgcgggagg agcagttcaa cagcacgtac cgtgtggtca gcgtcctcac cgtcctgcac 2340
caggactggc tgaacggcaa ggagtacaag tgcaaggtct ccaacaaagg cctcccgtcc 2400
tccatcgaga aaaccatctc caaagccaaa gggcagcccc gagagccaca ggtgtacacc 2460
ctgcccccat cccaggagga gatgaccaag aaccaggtca gcctgacctg cctggtcaaa 2520
ggcttctacc ccagcgacat cgccgtggag tgggagagca atgggcagcc ggagaacaac 2580
tacaagacca cgcctcccgt gctggactcc gacggctcct tcttcctcta cagcaggcta 2640
accgtggaca agagcaggtg gcaggagggg aatgtcttct catgctccgt gatgcatgag 2700
gctctgcaca accactacac acagaagagc ctctccctgt ctctgggtaa atga 2754

<210> SEQ ID NO 26
<211> LENGTH: 917
<212> TYPE: PRT
<213> ORGANISM: Homo sapiens

<400> SEQUENCE: 26

Met Val Leu Leu Trp Cys Val Val Ser Leu Tyr Phe Tyr Gly Ile Leu
1 5 10 15

Gln Ser Asp Ala Ser Glu Arg Cys Asp Asp Trp Gly Leu Asp Thr Met
20 25 30

Arg Gln Ile Gln Val Phe Glu Asp Glu Pro Ala Arg Ile Lys Cys Pro
35 40 45

Leu Phe Glu His Phe Leu Lys Phe Asn Tyr Ser Thr Ala His Ser Ala
50 55 60

Gly Leu Thr Leu Ile Trp Tyr Trp Thr Arg Gln Asp Arg Asp Leu Glu
65 70 75 80

Glu Pro Ile Asn Phe Arg Leu Pro Glu Asn Arg Ile Ser Lys Glu Lys

-continued

```
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510
```

-continued

```
Leu Leu Asp Lys Asp Asn Glu Lys Phe Leu Ser Val Arg Gly Thr Thr
        515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
        595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Glu Ser Lys Tyr Gly Pro Pro Cys Pro Pro Cys Pro Ala Pro Glu Phe
    690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
        755                 760                 765

Thr Tyr Arg Val Val Ser Val Leu Thr Val Leu His Gln Asp Trp Leu
    770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
        835                 840                 845

Val Glu Trp Glu Ser Asn Gly Gln Pro Glu Asn Asn Tyr Lys Thr Thr
    850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915
```

IL-1 ANTAGONIST FORMULATIONS

CROSS-REFERENCE TO RELATED APPLICATIONS

This application is a continuation-in-part application of U.S. Ser. No. 11/205,935 filed 17 Aug., 2005, now U.S. Pat. No. 7,365,165, which claims the benefit under 35 USC § 119(e) of U.S. Provisional 60/602,137 filed 17 Aug. 2004, which applications are herein specifically incorporated by reference in their entirety.

BACKGROUND OF INVENTION

1. Field of the Invention

The present invention is directed to pharmaceutical formulations comprising agents capable of inhibiting interleukin-1 (IL-1), and to methods for making and using such formulations. The invention is directed to pharmaceutical formulations having increased stability.

2. Statement of Related Art

Interleukin-1 (IL-1) antagonists capable of blocking or inhibiting the biological action of IL-1, have been described. An example IL-1 antagonist, an IL-1 trap, is described in U.S. Pat. No. 6,927,044, herein specifically incorporated by reference in its entirety. The term "IL-1 trap" refers to an IL-1-binding fusion protein comprising a dimer of two fusion proteins, each having two IL-1 receptor components and a multimerizing component.

Lyophilization (freeze-drying under controlled conditions) is commonly used for long term storage of proteins. The lyophilized protein is substantially resistant to degradation, aggregation, oxidation, and other degenerative processes while in the freeze-dried state (see, for example, U.S. Pat. No. 6,436,897).

BRIEF SUMMARY OF THE INVENTION

Stable formulations of an interleukin-1 (IL-1) antagonist are provided. The stable formulations comprise an IL-1-binding protein with a pharmaceutically acceptable carrier. In specific embodiments, liquid and freeze-dried, or lyophilized formulations are provided.

In one aspect, a pre-lyophilization formulation of an interleukin-1 (IL-1) antagonist is provided, comprising an IL-1 protein antagonist capable of binding to and inhibiting the biological action of IL-1, a buffer, an organic co-solvent or bulking agent, and one or more lyoprotectants. In a specific embodiment, the IL-1 antagonist is a fusion protein capable of binding to IL-1, the buffer is histidine, the organic co-solvent or bulking agent is polyethylene glycol (PEG), and the lyoprotectant(s) is at least one of glycine, arginine, and sucrose. In one embodiment, the pre-lyophilized formulation does not contain a preservative.

In one embodiment of the pre-lyophilization formulation, the formulation comprises 5-100 mM histidine, 0.5-3.0% PEG, 0.25-3.0% glycine, 5-50 mM arginine, 0.5-30.0% sucrose, and 5-50 mg/ml of an IL-1 antagonist, at a pH of about 6.5. In one embodiment, the pre-lyophilization formulation may further comprise up to 5 mM citrate and/or 0.003-0.005% polysorbate. The polysorbate may be, for example, polysorbate 20 or 80.

In a more specific embodiment, a pre-lyophilization IL-1 antagonist formulation is provided that consists essentially of about 25 mg/ml IL-1 trap protein (SEQ ID NO:10), 10-15 mM histidine, 0.8-1.0% PEG, 0.25-0.5% glycine, 15-20 mM arginine, and 0.5-1.0% sucrose. In a preferred embodiment, the formulation consists of 12.5 mM histidine, 0.94% PEG 3350, 0.31% glycine, 15.63 mM arginine, 0.63% sucrose, and 25 mg/ml of the IL-1 fusion protein having the sequence of SEQ ID NO:10, at a pH of about 6.5. In a specific embodiment, the pre-lyophilization formulation does not contain a preservative, a phosphate buffer, or more than trace amounts of NaCl. Citrate may be present in amounts of less than about 0.15 mM and up to about 0.005-0.01% polysorbate 20 may also be present.

In another aspect, a method of producing a lyophilized formulation of an IL-1 antagonist is provided, comprising subjecting a pre-lyophilization IL-1 antagonist formulation of the invention to lyophilization to generate a lyophilized IL-1 antagonist formulation. The lyophilized formulation may be lyophilized by any method known in the art for lyophilizing a liquid.

In a preferred embodiment, the lyophilization process comprises the steps of (i) cooling at 5° C.; (ii) freezing at −40° C.; (iii) annealing at −8° C.; (iv) freezing at −40° C.; (v) drying at 10° C.; (vi) drying at 40° C.; and (vii) cooling at 25° C. In a more specific embodiment, step (i) cooling is conducted for about 60 min; step (ii) freezing is conducted for about 120 min; step (iii) annealing is conducted for about 150 min; step (iv) freezing is conducted for about 120 min; step (v) drying is conducted for about 30 h; step (vi) drying is conducted for about 4 h; and/or step (vii) cooling is conducted for about 4 h.

In a more specific embodiment, a 25 mg/ml formulation of IL-1 trap protein is lyophilized as follows: vials containing the prelyophilized formulation are placed on precooled shelf at 5° C. and held at 5° C. for 60 min; temperature is ramped at 0.5° C./min to −40° C. and held at −40° C. for 120 min; temperature is ramped 0.5° C./min to −8° C. and held at −8° C. for 150 min; temperature is ramped at 0.5° C./min to −40° C. and held at −40° C. for 120 min; a vacuum is applied of 100 mTorr at a shelf temperature of −40° C.; temperature is ramped at 0.5° C./min to 10° C. and held at 10° C. for 30 h; temperature is ramped at 0.7° C./min to 40° C. and held at 40° C. for 4 h; temperature is ramped at 2° C./min to 25° C. and held at 25° C. for 4 h. The vials may be stoppered under a 608 Torr anhydrous nitrogen gas pressure to conclude lyophilization.

In another aspect, a lyophilized IL-1 antagonist formulation is provided that is made by lyophilizing an aqueous solution comprising 25 mg/ml IL-1 trap protein (SEQ ID NO:10), 10-15 mM histidine, 0.8-1.0% PEG, 0.25-0.5% glycine, 15-20 mM arginine, and 0.5-1.0% sucrose. In a preferred embodiment the lyophilized IL-1 trap formulation is lyophilized by (i) cooling at 5° C. for 60 min; (ii) freezing at −40° C. for 120 min; (iii) annealing at −8° C. for 150 min; (iv) freezing at −40° C. for 120 min; (v) drying at 10° C. for 30 h; (vi) drying at 40° C. for 4 h; and (vii) cooling at 25° C. for 4 h.

In another aspect, a lyophilized formulation of an IL-1 protein antagonist is provided that is capable of being reconstituted in an aqueous liquid in less than about three and a half minutes. In one embodiment, the lyophilized formulation is reconstituted in about one minute or less. In a specific embodiment, the aqueous liquid is water.

In another aspect, a lyophilized formulation of an IL-1 antagonist is provided that is capable of being reconstituted in a liquid with shaking, wherein following reconstitution at least 90% of the IL-1 antagonist is present in its native form as measured by size exclusion high performance liquid chromatography (SE-HPLC). In one embodiment, following reconstitution with shaking, at least about 95% of the IL-1 antagonist is present in its native form as measured by SE-HPLC. In another embodiment, at least about 98% of the IL-1 antagonist is present in its native form as measured by SE-H PLC.

In one embodiment, the lyophilized formulation is capable of being reconstituted at room temperature in water with vigorous shaking. In one embodiment, the shaking is carried out by vigorously agitating a mixture of the lyophilized formulation and water so that the mixture visibly bubbles and/or foams. In one embodiment, at least about 90% of the IL-1 antagonist of the reconstituted formulation is present in its native form as measured by SE-HPLC. In another embodiment, at least about 95% of the IL-1 antagonist of the reconstituted formulation is present in its native form as measured by SE-HPLC. In a more specific embodiment, at least about 98% of the IL-1 antagonist of the reconstituted formulation is present in its native form.

In another aspect, a lyophilized IL-1 antagonist formulation in a single dose unit is provided, wherein the IL-1 antagonist comprises the amino acid sequence of SEQ ID N0:10, and the lyophilized formulation is provided in a sterile container suitable for reconstitution as a liquid formulation for a single parenteral administration. In one embodiment, the container is a 20 ml glass vial. In another embodiment, the lyophilized formulation comprises about 220 mg of the IL-1 antagonist suitable for reconstitution as a liquid formulation having about 160 mg of withdrawable IL-1 antagonist. In another embodiment, the single dose is provided in a container suitable for reconstituting the lyophilized formulation to a volume of about 2.3 milliliters. In another embodiment, the single dose is provided in container that allows for a withdrawable content of about 2 milliliters. In another embodiment, the single dose comprises about 160 mg of the IL-1 antagonist. In another embodiment, the single dose unit is reconstitutable with water to a volume of about 2 milliliters and a concentration of about 80 mg/ml of IL-1 antagonist, about 40 mM histidine, about 50 mM arginine, about 3.0% polyethylene glycol 3350 (w/v), about 2% sucrose, and about 1% glycine (w/v), at a pH of 6.5±0.3. In another embodiment, the single dose does not include a preservative.

In another aspect, the invention features a method of producing a reconstituted lyophilized formulation of an IL-1 protein antagonist, comprising reconstituting the lyophilized formulation of the invention to a reconstituted formulation. In one embodiment, the IL:−1 protein antagonist of the reconstituted formulation is present at a concentration that is at least 3 times the concentration of the IL-1 protein antagonist of the pre-lyophilized formulation. In a preferred embodiment, a 25 mg/ml IL-1 trap protein formulation is lyophilized and reconstituted to an 80 mg/ml IL-1 trap protein formulation. In a specific embodiment, the lyophilized formulation is reconstituted with sterile water suitable for injection. In one embodiment, the reconstitution liquid may be bacteriostatic water. Reconstitution may include any suitable method, for example, by shaking or swirling.

In a another aspect, the invention features a stable liquid formulation of an IL-1 antagonist, comprising an IL-1 antagonist protein capable of binding to and inhibiting the biological action of IL-1, a buffer, an organic co-solvent, and one or more thermal stabilizers. In a specific embodiment, the IL-1 antagonist is an IL-1 trap fusion protein as shown in SEQ ID NO:10. In one embodiment, the buffer is a phosphate buffer. In one embodiment, the organic co-solvent agent is PEG, preferably PEG 3350. In one embodiment, the thermal stabilizers are NaCl and/or sucrose. More preferably, the thermal stabilizers are both NaCl and sucrose.

In a specific embodiment, the stable liquid formulation of an IL-1 antagonist comprises 5-100 mM phosphate buffer, 0.5-3% PEG, 25-150 mM NaCl, 5-30% sucrose, 10-500 mg/ml of an IL-1 trap protein, at a pH of about 6-6.5. In a more specific embodiment, the stable liquid formulation of an IL-1 antagonist comprises 10 mM phosphate buffer, 3% PEG 3350, 50 mM NaCl, 5-20% sucrose, 12.5-50 mg/ml of an IL-1 trap protein, at a pH of about 6-6.5. Additionally, low or trace amounts of a citrate buffer or polysorbate may be present. The stable liquid formulation of the IL-1 antagonist exhibits little or no precipitation as determined by visual inspection after storage of a 50 mg/ml IL-1 trap formulation for up to about 29 months at 5° C. Further, little or no aggregation is observed as determine by size-exclusion chromatography, e.g., HPLC, after storage of a 50 mg/ml IL-1 trap formulation for up to about 24 months at 5° C.

Unless otherwise specified or apparent from the context, any feature of the invention can be used in conjunction with any other feature of the invention. Other objects and advantages will become apparent from a review of the ensuing detailed description.

DETAILED DESCRIPTION OF THE INVENTION

Figure 1:
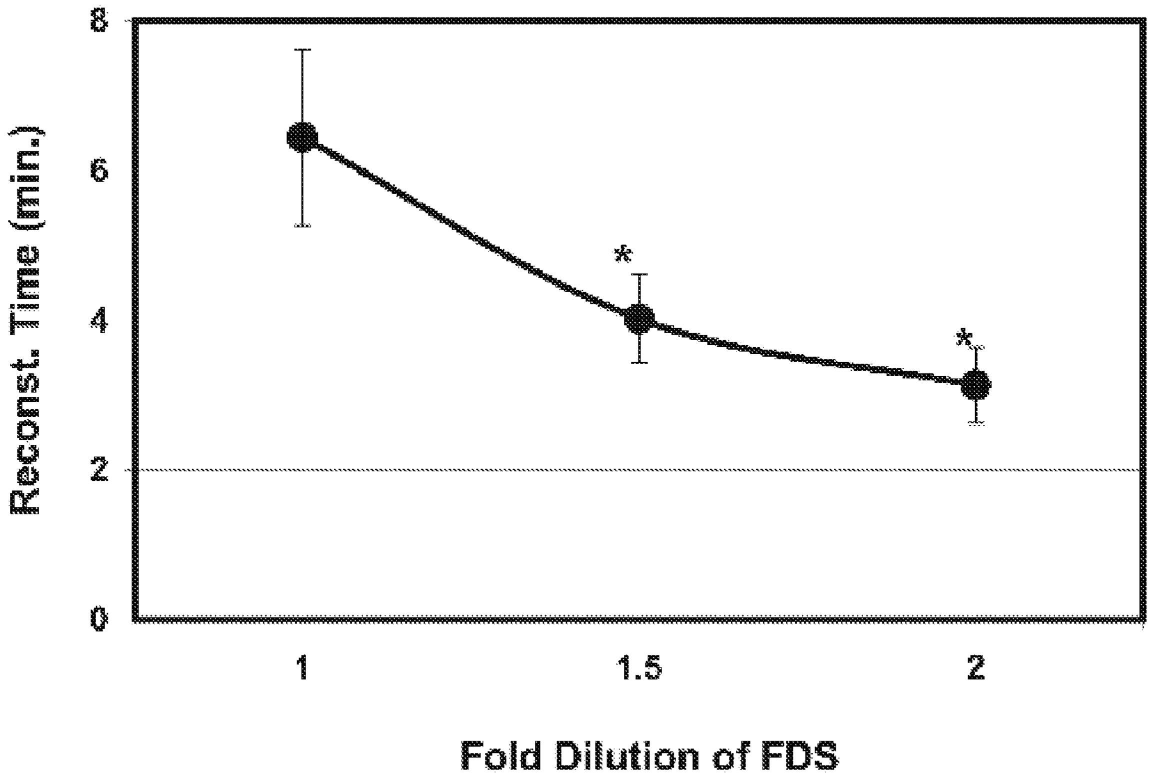
FIG. 1. Effect of dilution of pre-lyophilized IL-1 trap protein formulation on reconstitution time. IL-1 trap protein (SEQ ID NO:10) formulations were 40 mg/ml IL-1 trap protein, 20 mM histidine, 1.5% PEG 3350, 1% sucrose, 0.5% glycine, 25 mM arginine, pH 6.5 (control); 25 mg/ml IL-1 trap protein, 12.5 mM histidine, 0.94% PEG 3350, 0.63% sucrose, 0.31% glycine, 15.6 mM arginine, pH 6.5; and 20 mg/ml IL-1 trap protein, 10 mM histidine, 0.75% PEG 3350, 0.5% sucrose, 0.25% glycine, 12.5 mM arginine, pH 6.5. n=5. *$p<0.05$ vs. control, Student's t-test.

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure.

Unless stated otherwise, all technical and scientific terms and phrases used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference.

General Description

Safe handling and administration of formulations comprising proteins represent significant challenges to pharmaceutical formulators. Proteins possess unique chemical and physical properties that present stability problems: a variety of degradation pathways exist for proteins, implicating both chemical and physical instability. Chemical instability includes deamination, aggregation, clipping of the peptide backbone, and oxidation of methionine residues. Physical instability encompasses many phenomena, including, for example, aggregation.

Chemical and physical stability can be promoted by removing water from the protein. Lyophilization (freeze-drying under controlled conditions) is commonly used for long-term storage of proteins. The lyophilized protein is substantially resistant to degradation, aggregation, oxidation, and other degenerative processes while in the freeze-dried state. The lyophilized protein is normally reconstituted with water optionally containing a bacteriostatic preservative (e.g., benzyl alcohol) prior to administration.

DEFINITIONS

By the term "therapeutically or pharmaceutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the term "blocker", "inhibitor", or "antagonist" is meant a substance that retards or prevents a chemical or physiological reaction or response. Common blockers or inhibitors include, but are not limited to, antisense molecules, antibodies, antagonists and their derivatives.

The term "pharmaceutically acceptable" includes approval by a regulatory agency of the federal or a state government or listed in the U.S. Pharmacopeia or other generally recognized pharmacopeia for use in animals, and more particularly in humans.

The term "carrier" includes a diluent, adjuvant, excipient, or vehicle with which a composition is administered. Carriers can include sterile liquids, such as, for example, water and oils, including oils of petroleum, animal, vegetable or synthetic origin, such as, for example, peanut oil, soybean oil, mineral oil, sesame oil and the like.

The term "excipient" includes a non-therapeutic agent added to a pharmaceutical composition to provide a desired consistency or stabilizing effect. Excipients for parenteral formulations, include, for example, oils (e.g., canola, cottonseed, peanut, safflower, sesame, soybean), fatty acids and salts and esters thereof (e.g., oleic acid, stearic acid, palmitic acid), alcohols (e.g., ethanol, benzyl alcohol), polyalcohols (e.g., glycerol, propylene glycols and polyethylene glycols, e.g., PEG 3350), polysorbates (e.g., polysorbate 20, polysorbate 80), gelatin, albumin (e.g., human serum albumin), salts (e.g., sodium chloride), succinic acid and salts thereof (e.g., sodium succinate), amino acids and salts thereof (e.g., alanine, histidine, glycine, arginine, lysine), acetic acid or a salt or ester thereof (e.g., sodium acetate, ammonium acetate), citric acid and salts thereof (e.g., sodium citrate), benzoic acid and salts thereof, phosphoric acid and salts thereof (e.g., monobasic sodium phosphate, dibasic sodium phosphate), lactic acid and salts thereof, polylactic acid, glutamic acid and salts thereof (e.g., sodium glutamate), calcium and salts thereof (e.g., $CaCl_2$, calcium acetate), phenol, sugars (e.g., glucose, sucrose, lactose, maltose, trehalose), erythritol, arabitol, isomalt, lactitol, maltitol, mannitol, sorbitol, xylitol, nonionic surfactants (e.g., TWEEN 20, TWEEN 80), ionic surfactants (e.g., sodium dodecyl sulfate), chlorobutanol, DMSO, sodium hydroxide, glycerin, m-cresol, imidazole, protamine, zinc and salts thereof (e.g, zinc sulfate), thimerosal, methylparaben, propylparaben, carboxymethylcellulose, chlorobutanol, and heparin, The term "lyophilized" or "freeze-dried" includes a state of a substance that has been subjected to a drying procedure such as lyophilization, where at least 50% of moisture has been removed.

The phrase "bulking agent" includes a compound that is pharmaceutically acceptable and that adds bulk to a lyo cake. Generally, acceptable bulking agents known to the art include, for example, carbohydrates, including simple sugars such as dextrose, ribose, fructose and the like, alcohol sugars such as mannitol, inositol and sorbitol, disaccharides including trehalose, sucrose and lactose, naturally occurring polymers such as starch, dextrans, chitosan, hyaluronate, proteins (e.g., gelatin and serum albumin), glycogen, and synthetic monomers and polymers. In the formulations of the invention, PEG 3350 is an organic co-solvent which is used to stabilize the IL-1 protein antagonist when agitated, mixed, or handled, and as a bulking agent to help produce an acceptable bulk.

The term "lyoprotectant" includes a substance that may be added to a freeze-dried or lyophilized formulation to help maintain protein structure when freeze-dried or lyophilized.

A "preservative" includes a bacteriostatic, bacteriocidal, fungistatic or fungicidal compound that is generally added to formulations to retard or eliminate growth of bacteria or other contaminating microorganisms in the formulations. Preservatives include, for example, benzyl alcohol, phenol, benzalkonium chloride, m-cresol, thimerosol, chlorobutanol, methylparaben, propylparaben and the like. Other examples of pharmaceutically acceptable preservatives can be found in the USP.

IL-1 Antagonists

An IL-1 antagonist is a compound capable of blocking or inhibiting the biological action of IL-1, including fusion proteins capable of trapping IL-1, such as an IL-1 trap. In a preferred embodiment, the IL-1 trap is a dimer of two IL-1-specific fusion proteins, each comprising two IL-1 receptor components and a multimerizing component, for example, an IL-1 trap described in U.S. Pat. No. 6,927,044, issued Aug. 9, 2005, herein specifically incorporated by reference in its entirety. In a specific embodiment, the IL-1 trap is the fusion protein shown in SEQ ID NO:2, 4, 6, 8, 10, 12, 14, 16, 18, 20, 22, 24, 26. A preferred IL-1 trap is shown in SEQ ID NO:10. The invention encompasses the use of an IL-1 trap substantially identical to the protein of SEQ ID NO: 2, 4, 6, 8, 10, 12, 14, 16, 18, 20, 22, 24, 26, that is, a protein having at least 95% identity, preferably at least 97% identity, and more preferably at least 98% identity to the protein of SEQ ID NO: 2, 4, 6, 8, 10, 12, 14, 16, 18, 20, 22, 24, 26 and capable of binding and inhibiting IL-1. Further, in specific embodiments, the IL-1 antagonist is a modified IL-1 trap comprising one or more receptor components and one or more immunoglobulin-derived components specific for IL-1 and/or an IL-1 receptor. In another embodiment, the IL-1 antagonist is a modified IL-1 trap comprising one or more immunoglobulin-derived components specific for IL-1 and/or an IL-1 receptor.

In another embodiment, the IL-1 antagonist is an IL-1 trap that is a dimeric fusion protein having extracellular domains of human cytokine receptor IL-1 and the Fc portion of human IgG1 in a single dimeric molecule, wherein the extracellular domains are the IL-1 Type I recptor (IL-1 RI) and the IL-1 receptor accessory protein (AcP), wherein the dimer is covalently linked by disulfide bonds in the Fc region, and wherein the dimer has a molecular weight of about 252 kDa of which about 80% is protein (about 201 kDa) and about 20% is carbohydrate.

The IL-1 trap of the methods and formulations of the invention can be prepared by any suitable method known in the art, or that comes to be known, that is useful in preparing an IL-1 trap. The IL-1 trap is preferably substantially free of protein contaminants at the time it is used to prepare the pharmaceutically acceptable formulation. By "substantially free of protein contaminants" is meant, preferably, that at least 90% of the weight of protein of an IL-1 trap preparation used for making a formulation comprising an IL-1 trap is IL-1 trap protein, more preferably at least 95%, most preferably at least 99%. The IL-1 trap is preferably substantially free of aggregates. "Substantially free of aggregates" means that at least 90% of the weight of IL-1 trap protein is not present in an aggregate at the time the IL-1 trap is used to prepare the pharmaceutically effective formulation.

The IL-1 trap of the methods and formulations of the invention may contain low or trace amounts of compounds as a results of the purification process, for example, low or trace amounts of citrate and/or polysorbate. In one embodiment of the pre-lyophilization formulation of the invention containing about 40 mg of IL-1 trap/ml, citrate may be present at a concentration of about 0.1 mM and/or polysorbate may be present at a concentration of about 0.004%. If the pre-lyophilization formulation is reconstituted after lyophilization to half of the original volume (e.g., 80 mg/ml of IL-1 trap), the resulting concentrations may be 0.2 mM citrate and/or 0.008% polysorbate. If the pre-lyophilization formulation is reconstituted after lyophilization to a third of the original volume (e.g., 120 mg/ml of IL-1 trap), the resulting concentrations may be 0.6 mM citrate and/or 0.012% polysorbate.

Lyophilization and Lyophilized Formulations

In one aspect of the invention, a pharmaceutically acceptable formulation comprising an IL-1 trap is provided, wherein the formulation is a freeze-dried or lyophilized formulation. Preferably, the freeze-dried or lyophilized formulation comprises a pharmaceutically effective amount of an IL-1 trap. Lyophilized formulations can be reconstituted into solutions, suspensions, emulsions, or any other suitable form for administration or use. Lyophilized formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored at or below 30° C., for example, refrigerated at 4° C., or at room temperature (e.g., approximately 25° C.). Preferably, lyophilized formulations are stored below about 25° C., more preferably, at about 4-20° C.; below about 4° C.; below about −20° C.; about −40° C.; or about −70° C.

Lyophilized formulations are typically reconstituted for use by addition of an aqueous solution to dissolve the lyophilized formulation. A wide variety of aqueous solutions can be used to reconstitute a lyophilized formulation. Preferably, lyophilized formulations are reconstituted using water. Lyophilized formulations are preferably reconstituted with a solution consisting essentially of water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used.

Freeze-dried or lyophilized formulations are typically prepared from liquids, that is, from solutions, suspensions, emulsions, and the like. Thus, the liquid that is to undergo freeze-drying or lyophilization preferably comprises all components desired in a final reconstituted liquid formulation. As a result, when reconstituted, the freeze-dried or lyophilized formulation will render a desired liquid formulation upon reconstitution. A preferred liquid formulation used to generate a freeze-dried or lyophilized formulation comprises an IL-1 trap in a pharmaceutically effective amount, a buffer, a stabilizer, and a bulking agent. Freeze-dried or lyophilized formulations preferably comprise histidine, since histidine, in comparison to phosphate, is more effective at stabilizing the IL-1 trap when the IL-1 trap is lyophilized. Organic cosolvents, such as PEG 3350, are used to stabilize the IL-1 trap when agitated, mixed, or handled. A lyoprotectant is preferably used in freeze-dried or lyophilized formulations. Lyoprotectants help to maintain the secondary structure of proteins when freeze-dried or lyophilized. Three preferred example lyoprotectants are glycine, arginine, and sucrose, which are preferably used together.

EXAMPLES

Example 1

Stability of Pre-lyophilized and Lyophilized Formulations

The stability of pre-lyophilized and lyophilized formulations was determined. A pre-lyophilized formulation containing 40 mg/ml IL-1 trap (SEQ ID NO:10), 20 mM histidine, 1.5% PEG-3350, 1% sucrose, 0.5% glycine, 25 mM arginine-HCl, pH 6.5 was incubated at 5° C. for 0-52 weeks. As shown in Table 1, the native (non-aggregated) form of IL-1 decreased from 94.9 (0 weeks) to 92.3 (52 weeks), and the percent aggregate increased from 1% to 1.8% in the same time period.

TABLE 1

Stability of a Pre-Lyophilized Formulation

| Incubation time (weeks at 5° C.) | % Native | % Aggregate |
|---|---|---|
| 0 | 94.9 | 1.0 |
| 4 | 94.3 | 1.3 |
| 12 | 93.5 | 1.7 |
| 24 | 93.3 | 1.5 |
| 36 | 92.6 | 1.5 |
| 52 | 92.3 | 1.8 |

The stability of a lyophilized formulation containing 40 mg/ml IL-1 trap (SEQ ID NO:10), 20 mM histidine, 1.5% PEG-3350, 1% sucrose, 0.5% glycine, 25 mM arginine-HCl, pH 6.5 (pre-lyophilized concentrations) was incubated at 25° C. for 0-56 weeks. As shown in Table 2, the native (non-aggregated) form of IL-1 decreased from 97.0 (0 weeks) to 94.0 (56 weeks), and the percent aggregate increased from 0.8% to 3.6% in the same time period.

TABLE 2

| Stability of a Lyophilized Formulation | | |
|---|---|---|
| Incubation time (weeks at 25° C.) | % Native | % Aggregate |
| 0 | 97.0 | 0.8 |
| 3.9 | 96.3 | 1.4 |
| 6.1 | 95.5 | 1.5 |
| 12.3 | 95.4 | 1.9 |
| 25.7 | 94.7 | 2.2 |
| 39.3 | 94.4 | 2.9 |
| 56 | 94.0 | 3.6 |

Example 2

Effect of Drug Substance Concentration and Fill Volume on Reconstitution Time Experiments were undertaken to determine the effect of concentration of pre-lyophilized formulations of IL-1 antagonist on time required to reconstitute the final solution. A pre-lyophilized formula containing 40 ml IL-1 trap protein (SEQ ID NO:10) in 20 mM histidine at pH 6.5, 1.5% PEG 3350, 1% source, 0.5% glycine, 25 mM arginine-HCl (control) or diluted formulations were tested. A 1.6-fold dilution of the pre-lyophilization preparation from 40 mg/ml IL-1 trap protein to 25 mg/ml Il-1 trap protein was found to reduce reconstitution time by 36% without necessitating a lengthy freeze-drying process during lyophilization (FIG. 1).

Example 3

Effect of Lyophilization Methods on Reconstitution Time

The process of lyophilization was modified to include an annealing step to reduce the length of primary drying and eliminated crack development in the lyophilized cake. Optimization of the lyophilization process to reduce the length of the drying process included increasing the shelf temperature during primary and secondary drying steps. Product stability, final moisture content, and cake appearance were used to evaluate the feasibility of the different process conditions.

Freezing/Annealing. The process of annealing involves holding the frozen product above the glass transition temperature (Tg') of the formulation prior to the initiation of vacuum. Such a step may allow for crystal growth of excipients that did not fully crystallize during the initial freezing step, as well as reducing freezing-induced heterogeneity in drying rate through Ostwald ripening. Annealing has been reported to affect reconstitution times, secondary structure in the dried state, cracking in dried cakes, and aggregation of reconstituted product (see, for example, Webb et. al. (2003) J Pharmaceutical Sci 92:715-729).

Figure 2:
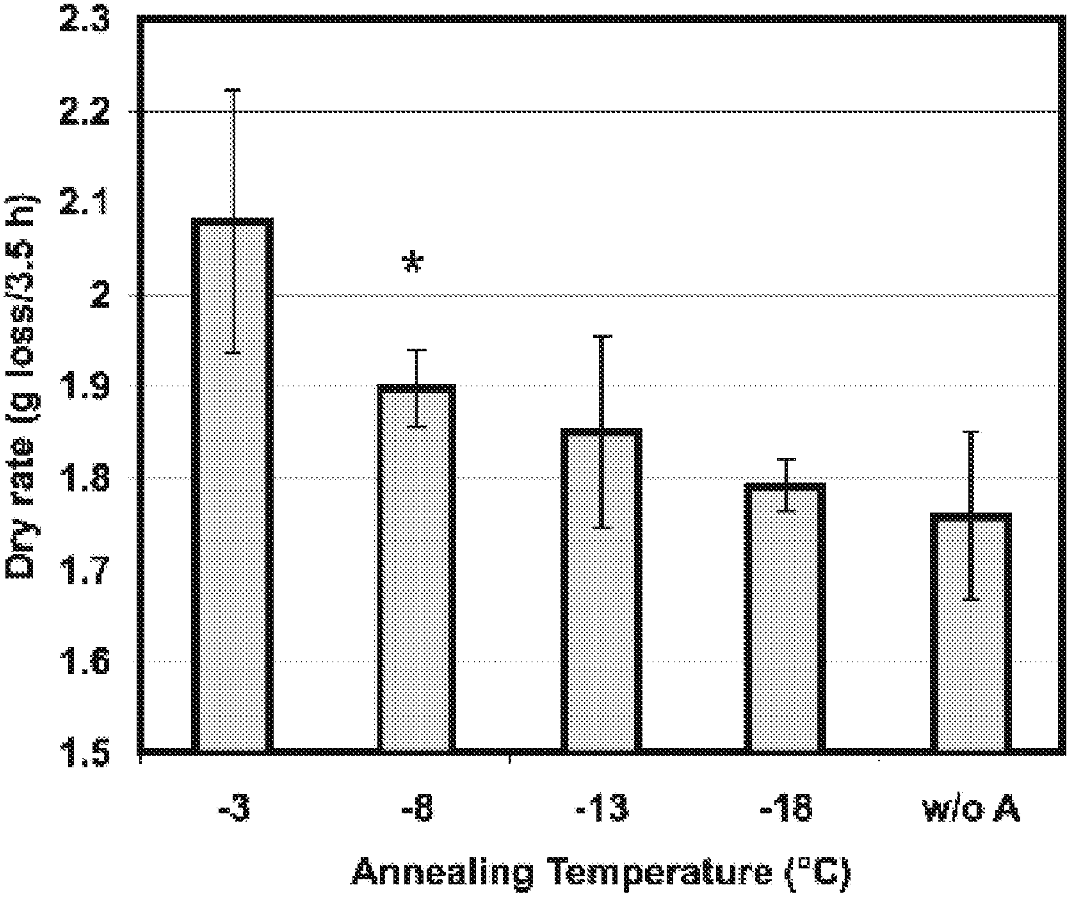
FIG. 2. Effect of annealing temperature on primary drying time of a 25 mg/ml IL-1 trap protein formulation (described above), n=5. Annealing hold time=3 hrs. Control=without annealing step. *One-way ANOVA test compared to control.

Annealing Temperature Optimization. Twenty ml vials were filled with 8.8 ml of 25 mg/ml IL-1 trap protein pre-lyophilization formulation and weighed. Sample vials were put in the freeze-dryer with a shelf temperature of 5° C. for 1 hour, frozen at −40° C. for 2 hours, annealed for 3 hours at either −3° C., −8° C., −13° C., or −18° C., and re-solidified at −40° C. for 1 hour. The shelf temperature ramp rate was 0.5° C./min in all of the above steps. The control unannealed sample vials were cooled and frozen as described above. All vials underwent primary drying in the same cycle. At the completion of the annealing step, all control and annealing test vials were transferred to the −40° C. shelf in the freeze-dryer for 1 hour as described above. Sublimation was initiated by first reducing the chamber pressure to 100 mTorr and then raising the shelf temperature to −5° C. Vials were stoppered after 5.5 h, during which 20-50% of the crystalline water has sublimed. The vials were re-weighed on removal from the freeze-dryer, and the primary drying rate was calculated using the weight lost during the partial drying. Compared to control vials without annealing or annealing at −13° C. or −18° C., cycles incorporating annealing steps at −3° C. or −8° C. had a significantly higher rate of sublimation (FIG. 2).

Figure 3:
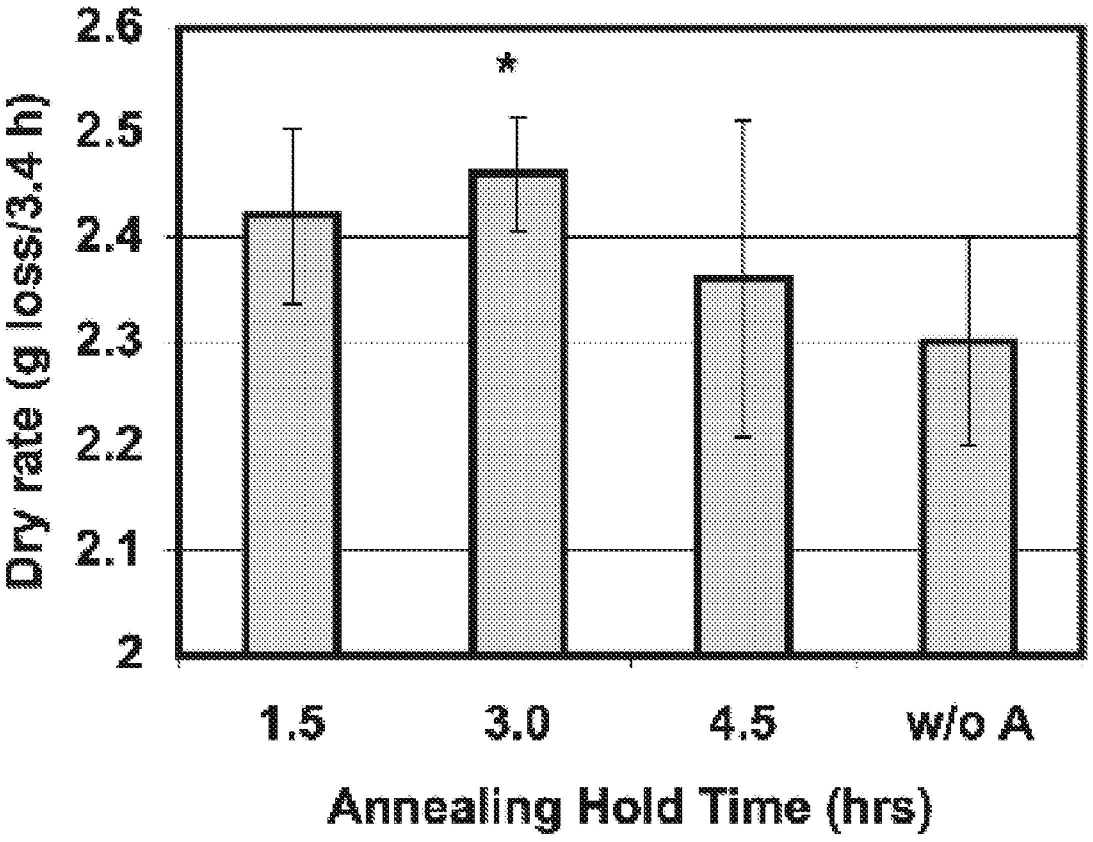
FIG. 3. Effect of annealing time on rate of primary drying. n=5. *$p<0.05$ one-way ANOVA test compared to control.

Annealing Time Optimization. Twenty ml vials were filled with 8.8 ml of 25 mg/ml IL-1 trap protein pre-lyophlization formulation and weighed. Sample vials were put in the freeze-dryer with a shelf temperature of 5° C. for 1 hour, frozen at −40° C. for 2 hr, annealed at −6° C. for either 1.5 hours, 3 hours, or 4 hours, and re-solidified at −40° C. for 1 h. The shelf temperature ramp rate was 0.5° C./min in all of the above steps. The control unannealed samples vials were cooled and frozen as described above. Sublimation was initiated by first reducing the chamber pressure to 100 mTorr and then raising the shelf temperature to −5° C. Vials were stoppered after 5.5 h. The vials were re-weighed on removal from the freeze-dryer, and the primary drying rate was calculated using the weight lost during the partial drying. Compared to the control that had no annealing step, only the 3 hour annealing step had a significant lowering of the sublimation rate (FIG. 3). An annealing time of 2.5 hours was chosen. The incorporation of this annealing step (−8° C. hold for 2.5 hours) in the lyophilization cycle resulted in vials that can be reconstituted in −60% of the time required to reconstitute the vials lyophilized without the annealing step. Combining the dilution of the pre-lyophilization formula and the incorporation of the annealing step shortened the reconstitution time of the resulting cake regardless of the method employed for reconstitution, as well as eliminating deep cracks in the resulting freeze-dried cakes.

Primary Drying. To determine the target product temperature for primary drying, the glass transition temperature (Tg') was determined to be −20° C. by subambient modulated differential scanning calorimetry (mDSC). The collapse temperature (Tc) is determined by freeze-drying microscopy. A maximum allowable product temperature of −23° C. was selected to provide a 3° C. safety margin during primary drying.

Secondary Drying. The chamber pressure was fixed at 100 mTorr for development of this lyophilization cycle. Although the length of secondary drying time is important for lowering moisture, the shelf temperature may be more important (see, for example, Pikal, "Freeze-Drying of Proteins Part 1: Process Design", Biopharm, September 1990.). A 25° C. shelf temperature was examined as a conservative but likely viable secondary drying step, while the secondary drying step of 40° C. was examined as a faster cycle due to decreased overall drying time. Secondary drying at both shelf temperatures met the target moisture content of less than 1% by Karl Fischer titration. In addition, the stability of the products generated from the 2 different secondary drying shelf temperatures was not significantly different. A similar amount of degradation was observed when lyophilized Drug Product produced from both secondary drying temperatures was stored at 50° C. or 40° C. for 4 weeks. No impact on the reconstitution time, pH, moisture content, or quality of the cake was observed. Therefore, a shelf temperature for secondary drying of 40° C. was chosen to shorten the length of secondary drying and the overall length of the cycle. Accordingly, the optimized lyophilization cycle, having a total time of approximately 52 hours, contained the following steps: (1) Cool: vials containing the prelyophilized formulation are placed on precooled shelf at 5° C. and held at 5° C. for 60 min; (2) Freeze: temperature is reduced 0.5° C./min to −40° C. and held at −40° C. for 120 min; (3) Anneal: temperature is increased 0.5° C./min to −8° C. and held at −8° C. for 150 min; (4)

Freeze: temperature is reduced 0.5° C./min to −40° C. and held at −40° C. for 120 min; (5) drying by applying a vacuum of 100 mTorr at a shelf temperature of −40° C.; (6) Primary drying: temperature changed 0.5° C./min to 10° C. and held at 10° C. for 30 h; (7) Secondary drying: temperature changed 0.7° C./min to 40° C. and held at 40° C. for 4 h; (8) Cooling secondary drying: temperature changed 2° C./min to 25° C. and held at 25° C. for 4 h.

The physical attributes of the lyophilized product examined were cake appearance, moisture, crystallinity, melting temperature (Tm), reconstitution time and turbidity of reconstituted solution. In addition, maintenance of secondary structure in the dried state compared to liquid was monitored by FTIR analysis. Cake appearance was recorded via a digital photograph of representative vials. No cracks were visible, no collapse of the cake occurred, and no meltback was observed. The moisture content was less than 0.1%. Polarized light microscopy was employed to assess the physical form of the drug product. The freeze-dried product showed no birefringence, indicating the absence of crystallinity. The control, LiCl powder showed birefringence as a typical crystalline solid. Analysis by modulated differential scanning calorimetry (mDSC), showed a thermal transition at approximately 56° C. The same signal has also been reported from other PEG-containing products and is believed to correspond to the phase transition of PEG. After reconstitution with 2.3 ml sterile water for injection, no significant increase in turbidity was measured at 405 nm, indicating no significant particulates were produced during the lyophilization and reconstitution processes. IL-1 trap protein remained stable during lyophilization and reconstitution. Purity, as determined by SE-HPLC (size exclusion high performance liquid chromatography) and non-reducing SDS-PAGE indicated only a slight increase in aggregate, that may be within the experimental error of the gel scanning equipment, compared to prelyophilization liquid. FTIR spectra in the amide I region of the prelyophilized and reconstituted product were superimposable, indicating the secondary structure was maintained through the lyophilization and the reconstitution processes.

Effect of Shaking on Reconstitution Time. Following addition of liquid, reconstitution by shaking resulted in the rapid reconstitution of the lyophilized product to the 80 mg/ml IL-1 trap protein formulation (Table 3). Reconstitution was performed by shaking the vial until the cake was completely reconstituted. Compared to the lyophilized 40 mg/ml IL-1 trap protein formulation, reconstitution of the lyophilized 25 mg/ml IL-1 trap protein formulation not only reduced the average reconstitution time but reduced the variability in the reconstitution times. The reduced variability is observed in a lower standard deviation and in a reduction in the difference observed between the maximum and minimum reconstitution times.

TABLE 3

Reconstitution Time as a Function of Concentration of Pre-Lyophilization Formula IL-1 Trap Formulation.

| FORMULATION/ DOSE FORM | 40 mg/ml FORMULATION (n = 20) | 25 mg/ml FORMULATION (n = 20) |
|---|---|---|
| Reconstitution Time | 97 ± 50 sec | 23 ± 6 sec |
| Maximum Time | 3 min 20 sec | 36 sec |
| Minimum Time | 49 sec | 11 sec |

Reconstituted products were analyzed by SE-HPLC and FTIR (Tables 4 and 5). Reconstitution by the shaking method had no detrimental effect on either the recovery of the protein or the purity as determined by SE-HPLC. The stability of reconstituted product also examined when reconstituted by vigorous shaking. This process involved shaking the vials as hard as possible, holding the top and bottom of the vial between two fingers. Despite the vigorous shaking, no significant increase in molecular weight variants was observed as determined by SE-HPLC analysis. No differences are observed in the stability of the product when reconstituted by either the swirling or shaking methods. In addition, FTI R analysis showed no differences in the secondary structure of IL-1 trap protein due to a reconstitution method (*Recovery determined by SE-HPLC).

TABLE 4

Reconstitution of Lyophilized 40 mg/ml IL-1 Trap Protein

| | RECONSTITUTION METHOD | | | | | |
|---|---|---|---|---|---|---|
| | SWIRLING | | SHAKING | | VIGOROUS SHAKING | |
| | Protein Recovered (mg/ml)* | % Native Remaining (SE-HPLC) | Protein Recovered (mg/ml)* | % Native Remaining (SE-HPLC) | Protein Recovered (mg/ml)* | % Native Remaining (SE-HPLC) |
| Pre-Lyo | 38 | 96.7 | 38 | 96.7 | 37 | 96.8 |
| Post-Lyo | 79 | 96.2 | 86 | 96.4 | 79 | 96.6 |

TABLE 5

Reconstitution of Lyophilized 25 mg/ml IL-1 Trap Protein

| | RECONSTITUTION METHOD | | | |
|---|---|---|---|---|
| | SWIRLING | | SHAKING | |
| | Protein Recovered (mg/ml)* | % Native Remaining (SE-HPLC) | Protein Recovered (mg/ml)* | % Native Remaining (SE-HPLC) |
| Pre-Lyo | 24 | 96.7 | 24 | 96.7 |
| Post-Lyo | 78 | 96.8 | 80 | 96.1 |

Reconsititution of lyophilized IL-1 trap using either the shaking or swirling methods had no adverse effect on the integrity of the protein, as determined by quantitative scan and visual inspection of Coomassie-stained non-reducing SDS-PAGE gels, and by measurement of IL-1 trap potency in a bioassay and in a binding assay. Oligosaccharide profiling assays showed no difference in sialic acid composition of the IL-1 trap between reconstitution by swirling and reconstitution by shaking. FTIR analysis of a pre-lyophilized preparation and reconstituted samples prepared by the swirling method and the shaking method showed no significant differences in the FTIR spectrum (about 1700 to about 1600 $cm^{-1}$), including in the amide I region.

Example 4

Stable Liquid Formulations

In one aspect, the invention provides a stable pharmaceutically acceptable formulation comprising an IL-1 trap, wherein the formulation is a liquid formulation. Preferably, the liquid formulation comprises a pharmaceutically effective amount of an IL-1 trap. The formulation can also comprise one or more pharmaceutically acceptable carriers, buffers, bulking agents, stabilizers, preservatives, and/or excipients. An example of a pharmaceutically acceptable liquid formulation comprising an IL-1 trap comprises an IL-1 trap in a pharmaceutically effective amount, a buffer, a co-solvent, and one or more stabilizers.

A preferred liquid formulation comprises phosphate buffer, an organic co-solvent, and one or more thermal stabilizers to minimize formation of aggregates and low molecular weight products when stored, and about 12.5 mg/ml to about 50 mg/ml IL-1 trap, wherein the formulation is from about pH 6.0 to about pH 6.75. A more preferred liquid formulation comprises 10 mM phosphate buffer, 3% PEG, 50 mM NaCl, 5-20% sucrose, and 10-100 mg/ml IL-1 trap, wherein the formulation is at a pH of about 6.0 to about 6.5. Although either NaCl or sucrose can be used as a stabilizer, a combination of NaCl and sucrose has been established to stabilize the IL-1 trap more effectively than either individual stabilizer alone. Preferably, PEG is PEG 3350, which has been established to enhance IL-1 trap stability.

Table 6 shows the percent of native IL-1 trap or percent aggregated IL-1 trap in samples containing either 5 or 20% sucrose as determined over a period of up to 24 months when incubated at 5° C. In the presence of 20% sucrose, the native (non-aggregated) form of IL-1 trap dropped from 92.6% at day 0 to 88.9% at 24 months and the percentage aggregate increased from 2.3% to 3.4% over the same time period. The 5% sucrose formulation had a native (non-aggregated) form of IL-1 trap dropped from 92.4% at day 0 to 86.9% at 24 months and the percentage aggregate increased from 2.6% to 3.6% over the same time period.

TABLE 6

Native and Aggregate IL-1 Trap as a Function of Time and Sucrose at 5° C.

| | 20% Sucrose | | 5% Sucrose | |
|---|---|---|---|---|
| Incubation time at 5° C. (months) | Native (%) | Aggregate (%) | Native (%) | Aggregate (%) |
| 0 | 92.6 | 2.3 | 92.4 | 2.6 |
| 1.0 | 92.6 | 2.4 | 92.5 | 2.5 |
| 2.0 | 91.9 | 2.6 | 91.5 | 2.9 |
| 6.0 | 91.6 | 2.8 | 91.0 | 2.9 |
| 18 | 91.8 | 3.2 | 90.7 | 3.6 |
| 21.0 | 91.3 | 2.9 | 89.5 | 3.6 |
| 24.0 | 88.9 | 3.4 | 86.9 | 3.6 |

Table 7 shows the percent of native IL-1 trap in samples containing either 0, 5 or 20% sucrose as determined over a period of up to 2.9 months when incubated at 5° C. (50 mg/ml IL-1 trap, 10 mM Phosphate, 0.2% polysorbate-20, 50 or 135 (with 0% sucrose) mM NaCl, pH 6.5. In the presence of 0% sucrose, the native (non-aggregated) form of IL-1 trap dropped from 96.4% at day 0 to 0.5% at 2.9 months. The 5% sucrose formulation had a native (non-aggregated) form of IL-1 trap which dropped from 96.5% at day 0 to 39.2% at 2.9 months. The 20% sucrose formulation had a native (non-aggregated) form of IL-1 trap which dropped from 96.4% at day 0 to 95.3% at 2.9 months.

TABLE 7

% Native IL-1 Trap as a Function of Time and Sucrose Concentration at 5° C.

| Incubation Time | PERCENT NATIVE | | |
|---|---|---|---|
| (months) | 0% Sucrose | 5% Sucrose | 20% Sucrose |
| 0 | 96.4 | 96.5 | 96.4 |
| 1 | 96.7 | 89.3 | 96.2 |
| 2.9 | 0.5 | 39.2 | 95.3 |

Formulations, whether liquid or freeze-dried and lyophilized, can be stored in an oxygen-deprived environment. Oxygen-deprived environments can be generated by storing the formulations under an inert gas such as, for example, argon, nitrogen, or helium.

Although the foregoing invention has been described in some detail by way of illustration and examples, it will be readily apparent to those of ordinary skill in the art that certain changes and modifications may be made to the teachings of the invention without departing from the spirit or scope of the appended claims.

We claim:

1. A formulation of an interleukin-1 (IL-1) antagonist suitable for lyophilization, comprising about 25 mg/ml of an IL-1-binding fusion protein comprising the amino acid sequence of SEQ ID NO:10, 10-15 mM histidine, 0.8-1.0% PEG, 0.25-0.5% glycine, 15-20 mM arginine, and 0.5-1.0% sucrose.

2. The formulation of claim 1 reconstituted to 80 mg/ml IL-1 binding fusion protein.

3. A lyophilized formulation of an interleukin-1 (IL-1) antagonist comprising the amino acid sequence of SEQ ID NO:10, produced by lyophilizing an aqueous solution comprising 25mg/ml IL-1 antagonist, 10-15 mM histidine, 0.8-1.0% PEG, 0.25-0.5% glycine, 15-20mM arginine, and 0.5-1.0% sucrose.

4. The lyophilized formulation of claim 3, wherein lyophilization comprises the steps of:

(i) cooling at 5° C.;

(ii) freezing at −40° C.;

(iii) annealing at −8° C.;

(iv) freezing at −40° C.;

(v) drying at 10° C.;

(vi) drying at 40° C.; and (vii) cooling at 25° C.

5. The lyophilized formulation of claim 4, wherein step (i) cooling is conducted for about 60 min.

6. The lyophilized formulation of claim 4, wherein step (ii) freezing is conducted for about 120 min.

7. The lyophilized formulation of claim 4, wherein step (iii) annealing is conducted for about 150 min.

8. The lyophilized formulation of claim 4, wherein step (iv) freezing is conducted for about 120 min.

9. The lyophilized formulation of claim 4, wherein step (v) drying is conducted for about 30 h.

10. The lyophilized formulation of claim 4, wherein step (vi) drying is conducted for about 4 h.

11. The lyophilized formulation of claim 4, wherein step (vii) cooling is conducted for about 4 h.

12. The lyophilized formulation of claim 4, wherein step (i) cooling is conducted for about 60 min; step (ii) freezing is conducted for about 120 min; step (iii) annealing is conducted for about 150 min; step (iv) freezing is conducted for about 120 min; step (v) drying is conducted for about 30 h; step (vi) drying is conducted for about 4 h; and step (vii) cooling is conducted for about 4 h.

13. An interleukin-1 (IL-1) antagonist formulation reconstituted from the lyophilized formulation of claim 4.

14. The reconstituted IL-1 antagonist of claim 13, wherein the reconstituted formulation is at least 3 times the concentration of a lyophilized formulation.

15. The reconstituted IL-1 antagonist of claim 14 comprising 80 mg/ml IL-1 antagonist protein.

16. A lyophilized formulation of an interleukin-1 (IL-1) antagonist comprising the amino acid sequence of SEQ ID NO:10, produced by lyophilizing an aqueous solution comprising 25mg/ml IL-1 antagonist, 10-15mM histidine, 0.8-1.0% PEG, 0.25-0.5% glycine, 15-20mM arginine, and 0.5-1.0% sucrose, wherein lyophilization comprises the steps of:

(i) cooling at 5° C. for 60 min;

(ii) freezing at −40° C. for 120 min;

(iii) annealing at −8° C. for 150 min;

(iv) freezing at −40° C. for 120 min;

(v) drying at 10° C. for 30 h;

(vi) drying at 40° C. for 4 h; and (vii) cooling at 25° C. for 4 h.

17. An interleukin-1 (IL-1) antagonist formulation reconstituted from the lyophilized formulation of claim 16.

18. The reconstituted IL-1 antagonist of claim 17, wherein the reconstituted formulation is at least 3 times the concentration of a lyophilized formulation.

19. The reconstituted IL-1 antagonist of claim 18 comprising 80 mg/ml IL-1 antagonist protein.

* * * * *